United States Patent [19]
Meers et al.

[11] Patent Number: 6,087,325
[45] Date of Patent: Jul. 11, 2000

[54] PEPTIDE-LIPID CONJUGATES

[75] Inventors: Paul R. Meers, Princeton Junction; Charles Pak, Plainsboro; Shaukat Ali, Monmouth Junction, all of N.J.; Andrew Janoff, Yardley, Pa.; J. Craig Franklin, East Windsor, N.J.; Ravi K. Erukulla, Plainsboro, N.J.; Donna Cabral-Lilly, Lawrenceville, N.J.

[73] Assignee: The Liposome Company, Inc., Princeton, N.J.

[21] Appl. No.: 08/950,618

[22] Filed: Oct. 15, 1997

Related U.S. Application Data

[60] Provisional application No. 60/027,544, Oct. 15, 1996.

[51] Int. Cl.$^7$ .......................... A61K 38/00; A61K 9/127; C07K 5/00; C07K 7/00
[52] U.S. Cl. .................................. 514/2; 514/12; 514/16; 514/17; 514/18; 424/450; 530/324; 530/326; 530/327; 530/328; 530/387; 530/402
[58] Field of Search .................................. 514/2, 18, 16, 514/17; 424/450; 530/324, 326, 327, 328, 387, 402

[56] References Cited

U.S. PATENT DOCUMENTS

| | | | |
|---|---|---|---|
| 4,837,028 | 6/1989 | Allen et al. | 424/450 |
| 4,920,016 | 4/1990 | Allen et al. | 424/450 |
| 5,013,556 | 5/1991 | Woodle et al. | 424/450 |

OTHER PUBLICATIONS

Aimes, et al., "Matrix Metalloproteinase–2 is an Interstitial Collagenase," (1995), J. Biol. Chem., 270, 5872–5876.
Ascenzi, et al., "The Hydrolysis of α–CBZ–L–Lysine–p–Nitrophenyl Ester by Two Forms of Human Urokinase," Anal. Biochem., 103:235 (1980).
Barrett et al., "Cathespin B, Cathespin H, and Cathespin L," Meth. Enzymol. 80:535 (1981).
Bartlett, G. R., "Phosphorus Assay in Column Chromatography," (1959), J. Biol. Chem., 234, 466–468.
Berka, et al., "Adrenaline cells of the rat adrenal cortex and medulla containing renin and proreni," (1996) Molecular & Cellular Endocrinology 119, 175–184.
Blume et al., "Specific targeting with poly(ethylene glycol)–modified liposomes coupling of homing devices to the ends of the polymeric chains combines effective target binding with long circulation times," Biochim. Biophys. Acta 1149: 180 (1993).
Boyd, D., "Invasion and Metastasis [Review]", (1996) Cancer and Metastasis Reviews, 15, 77–89.
Castillo et al., "Sensitive Substrates for Human Leukocyte and Porcine Pancreatic Elastase: A Study of the Merits of Various Chromophoric and Fluorogenic Leaving Groups in Assays for Serine Proteases," Anal. Biochem 99;53 (1979).
Clague, et al., "Gating Kinetics of pH–Activated Membrane fusion of Vesicular Stomatits Virus with Cells: Stopped–Flow Measurements by Dequenching of Octadeyl-rhodaamine4 Fluorescence," (1990) Biochemistry 29, 1303–1309.

Davidson, et al., "Association and release of prostaglandin E1 from liposomes," Biochim. Biophys. Acta 1327, (1997), 97–106.
Fosang et al, "Neutrophil collagenase (MMP–8) Cleaves at the aggrecanase site $E^{373}$–$A^{374}$ in the interglobular domain of cartilage aggrecan," (1994) Biochemical J., 304, 347–351.
Froehlich, et al., "Human Granzyme B Degrade Aggrecan Proteoglycan in Matrix Synthesized by Chondrocytes," (1993) J. Immunol. 151, 7161–7171.
Gabison, et al., "Prolongation of the Circulation Time of Doxorubicin Encapsulated in Liposomes Containing a Polyethylene Glycol–Derivatized Phospholipid. Pharmacokinetc Studies in Rodents and Dogs," Pharm. Res. 10(5):703 (1993).
Hoog, et al., "Human Immunodeficiency Virus Protease Ligand Specificity Conferred by Residues Outside of the Active Site Cavity," Biochemistry 35, 10279–10286.
Johnson, et al., "Assay Methods and Standard Preparations for Plasmin, Plasminogen and Urokinase in Purified Systems, 1967–1968," Thromb. Diath. Haemorrh., 21, 259 (1969).
Kirschke et al; Action of rat liver cathepsin L on collagen and other substrates,: Biochem J. 201:367 (1982).
Knäuper et al., "Biochemical Characterization of Human Collagenase–3," (1996), J. Biol Chem, 271, 1544–1550.
Knight, "Human cathepsin B," Biochem, J. 189, 447 (1980).
Kossakowska, et al, "Comparative analysis of the expression patterns of metalloproteinases and their inhibitors in breast neoplasia, sporadic colorectal neoplasia, plumonary carcinomas and malignant non–Hodgkin's lymphomas in humans," (1996) Br. J. Cancer 73, 1401–1408.
Liotta, et al., "Cancer Metastasis and Angiogenesis: An Imbalance of Positive and Negative Regulation", (1991) Cell 64, 327–336.
Mayer, et al., (1986) Biochim. Biophys. Acta, 858, 161–168.
Moehrle, et al., "Aminopeptidase M and dipeptidyl peptidase IV activity in epithelial skin tumors: a histochemical study," (1995) J. Cutaneous Path, 22, 241–247.
Nagase et al., "Design and Characterization of a Fluorogenic Substrate Selectively Hydrolyzed by Stomelysin 1 (Matrix Metalloproteinase–3)," (1994) J. Biol. Chem. 269, 20952–20957.
Nakajima, et al., "Mapping the Extended Substrate Binding Site of Cathespin G and Human Leukocyte Elastase," (1979) J. Biol. Chem, 254, 4027–4032.

(List continued on next page.)

*Primary Examiner*—Avis M. Davenport
*Attorney, Agent, or Firm*—Rosanne Goodman

[57] ABSTRACT

Peptide-lipid conjugates are incorporated into liposomes so as to selectively destabilize the liposomes in the vicinity of target peptidase-secreting cells, and hence, to deliver the liposomes to the vicinity of the target cells, or directly into the cells. The liposomes can thus be used to treat mammals for diseases, disorders or conditions, e.g., tumors, microbial infection and inflammations, characterized by the occurrence of peptidase-secreting cells.

12 Claims, 16 Drawing Sheets

OTHER PUBLICATIONS

Odake, et al., "Human and Murine Cytotoxic T. Lymphocyte Serine Proteases: Subsite Mapping with Peptide Thioester Substrates and Inhibition of Enzyme Activity and Cytolysis by Isocoumarins," (1991) Biochemistry 30, 2217–2227.

O'Leary, et al., "A Study of a Synaptosomal Thyrotropin Releasing Hormone–inactivating Pyroglutamate Aminopeptidase from Bovine Brain," (1995) Int. J. Biochem, Cell Biol. 27, 881–890.

Palmieri, et al., "Dipeptidyl(amino)Peptidase IV and Post Proline Cleaving Enzyme in Sultured Endothelial and Smooth Muscle Cells," (1989) Adv. Exp. Med. Biol. 247A, 305–311.

Park, et al., "Some negatively charged phospholipid derivatives prolong the liposome circulation in vivo", (1992) Biophys Acta, 1108:257 (1992).

Pei, et al., "Hydrolytic Inactivation of a Breast Carcinoma Cell–derived Serpin by Human Stromelysin–3," (1994) J. Biol. Chem., 269–25849–25855.

Perkins, et al., "Combination of antitumor ether lipid with lipids of complementary molecular shape reduces its hemolytic activity", Biochim. Biophys. Acta, 1327 (1997), 61–68.

Petkov, et al., "Structure–Activity Relationship in the Urokinase Hydrolysis of $\alpha$–N–Acetyl–L–lysine Anilides," Eur. J. Biochem., 51:25 (1975).

Prechel, et al., "Effect of a New Aminopeptidase P Inhibitor, Apstatin on Bradykinin Degradation in the Rat Lung," (1995) J. Pharmacol. And Exp. Therapeutics 275, 1136–1142.

Rogi, et al., "Human Placental Leucine Aminopeptidase/Oxytocinase," (1996), J. Biol. Chem, 271, 56–61.

Sato, et al., "Site Specific Liposomes Coated with Polysaccharides," in: *Liposome Technology* (G. Gregoriadis, ed.,), CRC Press (Boca Raton, FL), 1993, pp. 179–198.

Spratt, et al, "*Capnocytophaga gingivalis* aminopeptidase: a potential virulence factor", (1995) Microbiology, 141, 3087–3093.

Steck, et al., "Preparation of Impermeable Ghosts and Inside Out Vesicles from Human Erythrocyte Membranes," (1974), Methods Enzymol. 31, 172–180.

Struck, et al., "Use of Resonance Energy Transfer to Monitor Membrane Fusion," (1981) Biochemistry 20, 4093–4099.

Subbaro, et al., "pH–Dependent Bilayer Destabilization by an Amphipathic Peptide," Biochem, 26(11):2964 (1987).

Unden, Et al., "Stromelysin–3 mRNA Associated with Myofibroblasts in Overexpressed in Aggressive Basal Cell Carcinoma and in Dermatofibroma but Not in Dermatofibrosarcoma," (1996), J. Invest. Dermat, 107, 147–153.

Vogel, et al., "Lysophosphatidylcholine Reversibly Arrests Exocytosis and Viral Fusion at a Stage between Triggering and membrane Merger", JBC 268:25764 (1993).

Ward et al, "Angiotensin and Bradykinin Metabolism by Peptidases Identified in Skeletal Muscle," (1995) Peptides, 16, 1073–1078.

Williamson, et al., "Phospholipid Asymmetry in Human Erythrocyte Ghosts", (1985) J. Cell Physiol, 123, 209–214.

Wilson, et al., "Hyperglycemia Induces a Loss of Phospholipid Asymmetry in Human Erythrocytes," (1993) Biochemistry 32, 11302–11310.

Wohl, et al., "Kinetics of Activation of Human Plasminogen by Different Activator Species at pH 7.4 and 37° C.," JBC, 255:2005 (1980).

Yamashita, et al., "Production of immunoreactive polymorphonuclear leucocyte elastase in human breast cancer cells; possible role of polymorphonuclear leucocyte elastase in the progression of human breast cancer," (1994) Br. J. Cancer 69, 72–76.

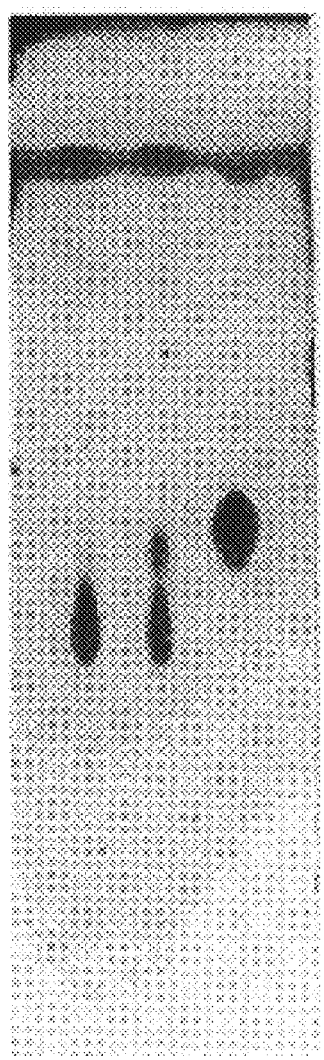
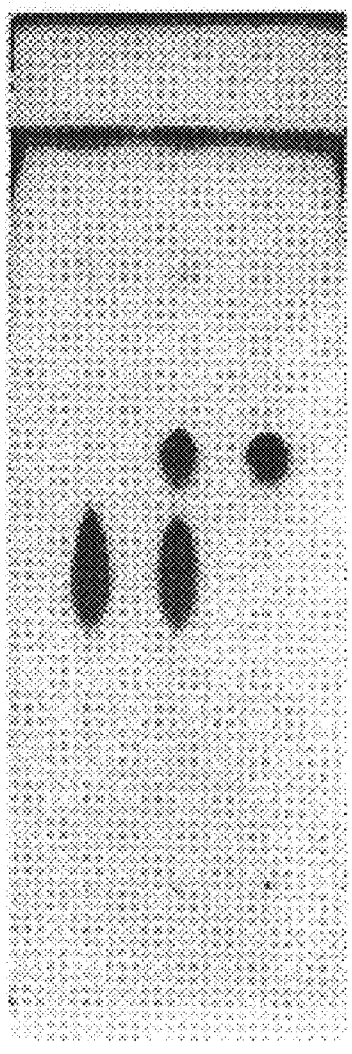
Fig. 2 A
Fig. 2 B
1　2　3
1　2　3

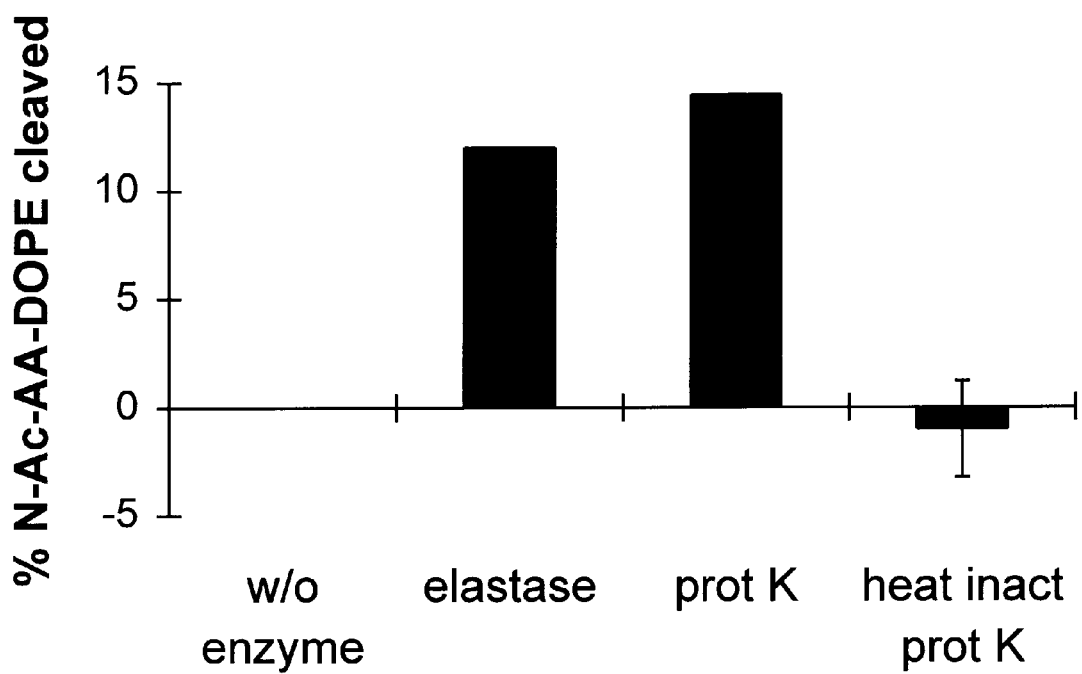

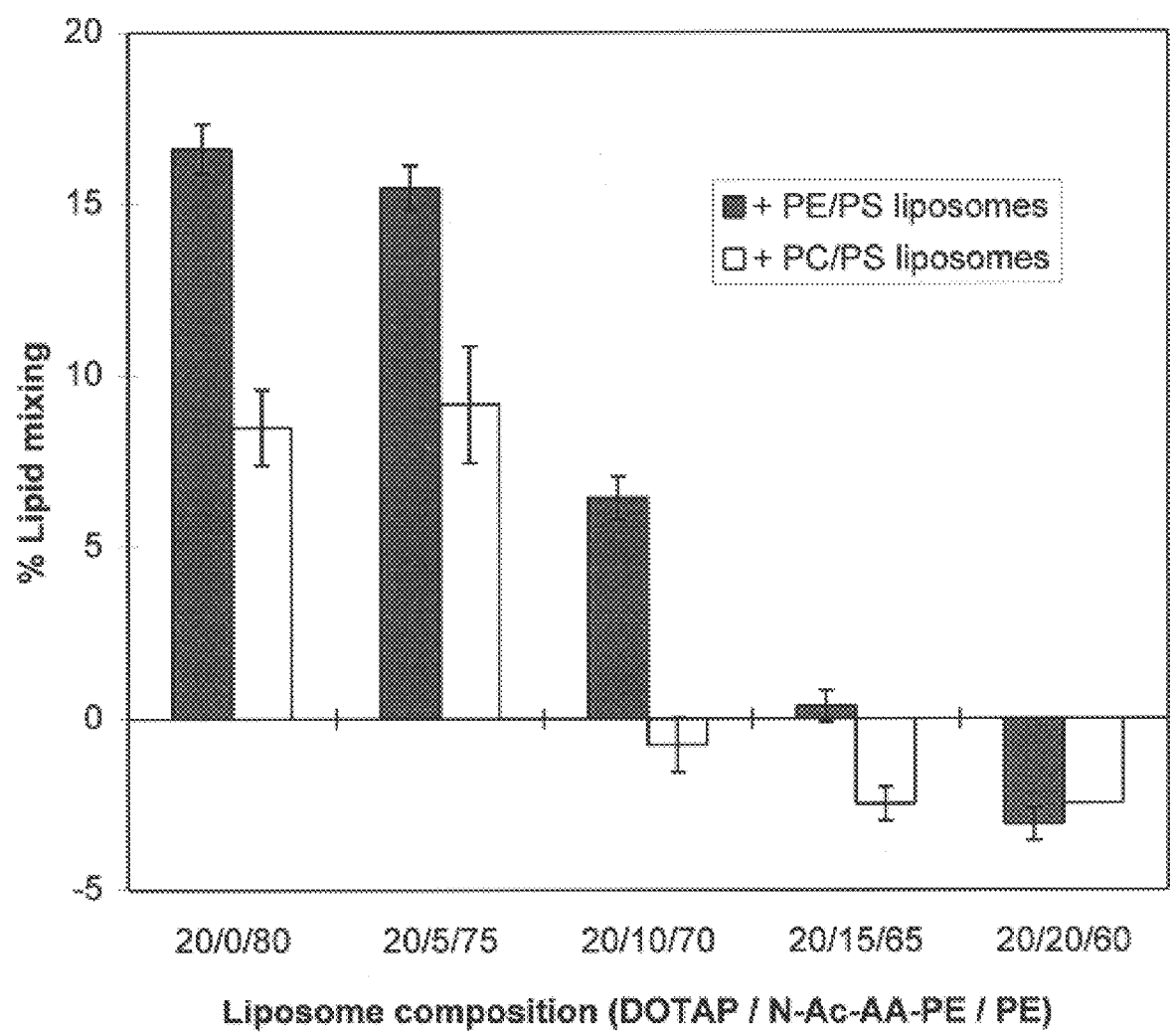

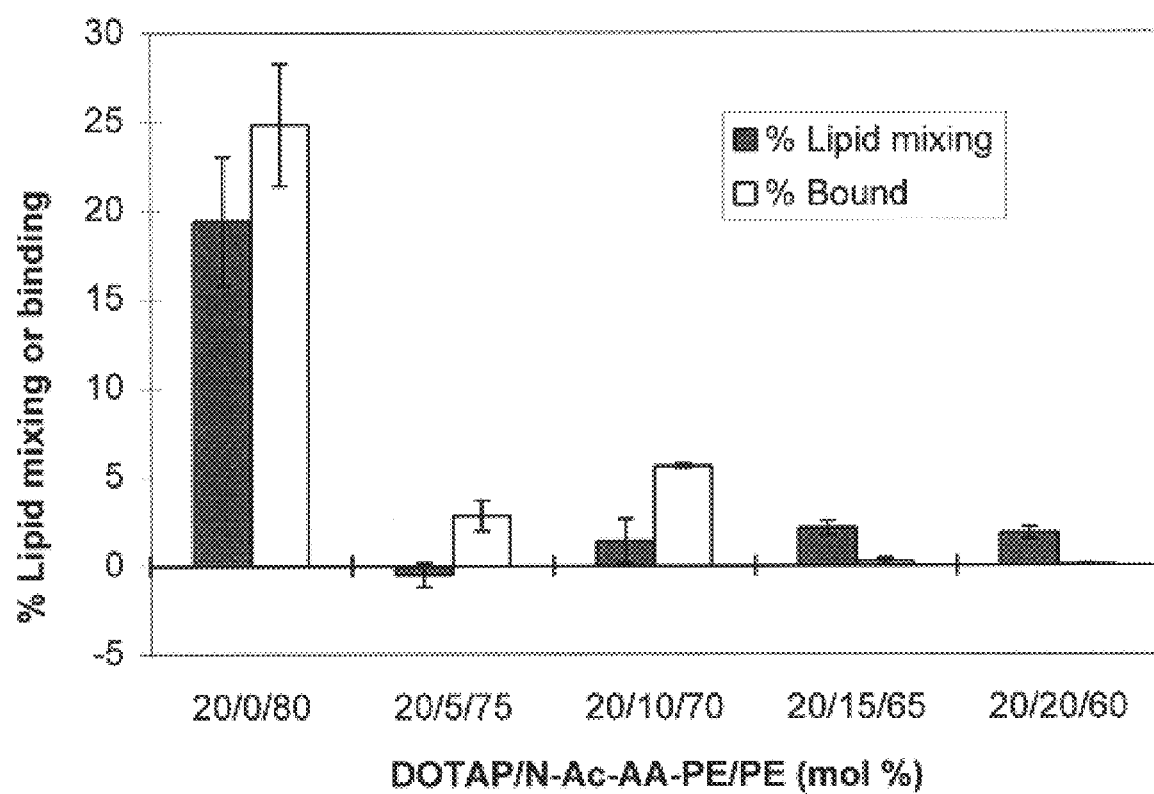

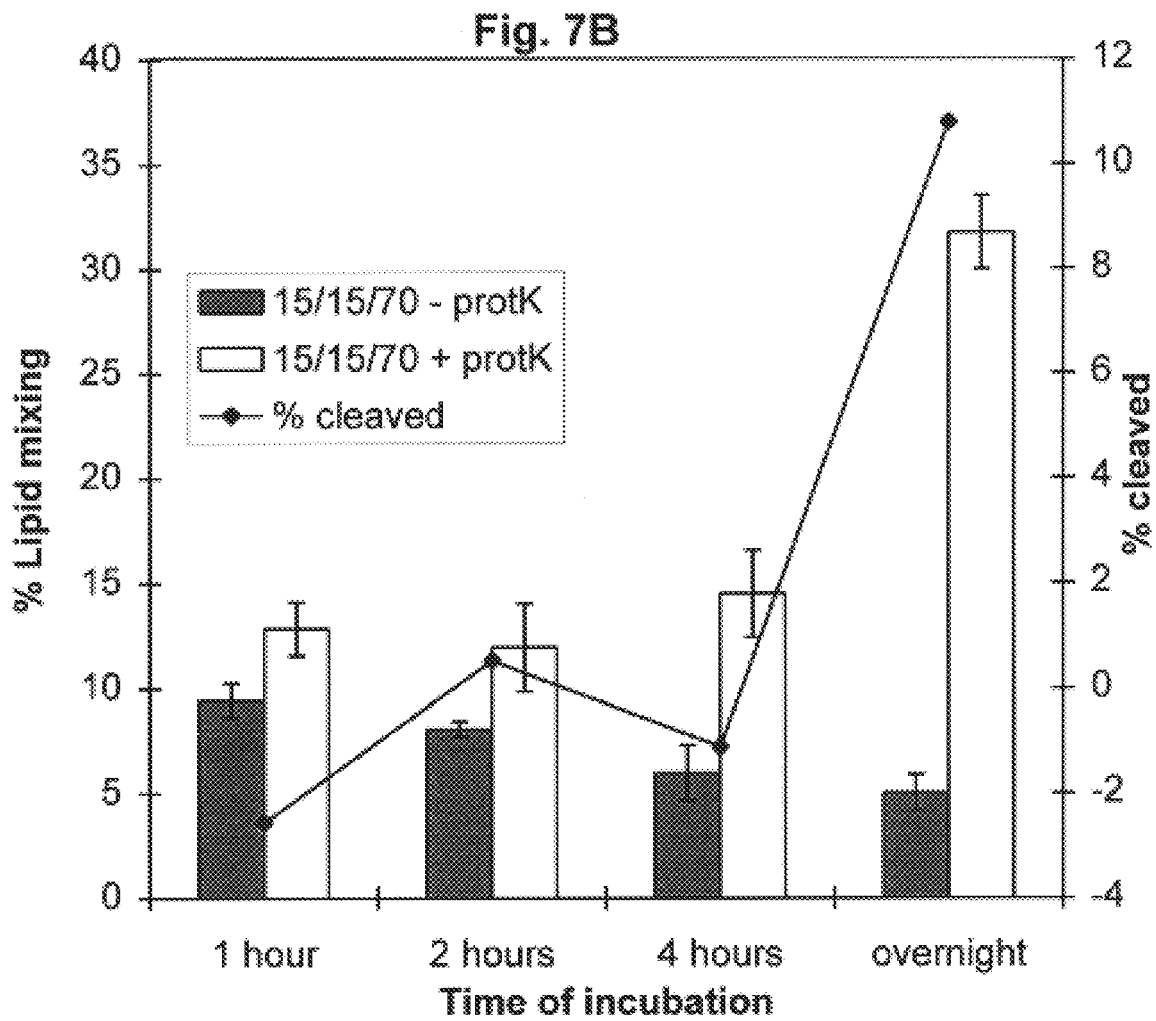

1 2 3 4   5 6 7 8

1 2 3 4  5 6 7 8

PEPTIDE-LIPID CONJUGATES

This application is a CIP of provisional application U.S. Ser. No. 60/027,544 filed Oct. 15, 1996.

FIELD OF THE INVENTION

Peptide-lipid conjugates are incorporated into liposomes so as to localize delivery of the liposomes' contents to the vicinity of target cells.

BACKGROUND OF THE INVENTION

Liposomes have been widely used as carriers to deliver a variety of therapeutic and diagnostic agents into cells. Encapsulation of active agents in liposomes protects the agents from premature degradation, and ameliorates side effects resulting from administration of the agents to animals (for a review, see, e.g., A. Bangham, 1992; M. Ostro, 1987; and, M. Ostro and P. Cullis, 1989). However, the efficiency of liposomal drug delivery has heretofore been constrained by the lack of a means of inducing liposomes to preferentially release their contents in the vicinity of, or into, target cells. This invention provides such a means, by incorporating peptide-lipid conjugates into liposomes and then contacting cells with these liposomes.

The lipid portion of the peptide-lipid conjugate is a phosphatidylethanolamine ("PE"). These lipids ordinarily do not organize into bilayers at neutral pH, instead forming hexagonal ($H_{II}$)-phase structures in aqueous environments which tend to destabilize the bilayers of liposomes into which the lipids have been incorporated. These same structures can also enhance the liposomes' fusogenicity (Verkleij, 1984; Cullis & de Kruijff, 1979; Ellens et al., 1989). Conjugation of a peptide to the PE stabilizes the PE in a bilayer conformation and hence, allows the conjugated lipid to be stably incorporated into liposome bilayers. However, once the peptide is cleaved, e.g., in the vicinity of peptidase-secreting cells, the lipid then resumes its nonbilayer-preferring, hexagonal conformation, in which it tends to destabilize the same liposome bilayers.

The peptide portion of the peptide-lipid conjugate is any of those peptides having amino acid sequences that are recognized and cleaved by any of the various peptidases secreted by mammalian cells, e.g., at sites of inflammation and tumor metastases (see, e.g. Aimes and Quigley, 1995; Fosang et al., 1994; Froelich et al., 1993; Knauper et al., 1996; Liotta et al., 1991; Moehrle et al., 1995; Nagase et al., 1994; Nakajima et al., 1979; Odake et al., 1991; Palmieri et al., 1989; Pei et al., 1994; Prechel et al., 1995; Yamashita et al., 1994). Neither linkage of peptidase-cleavable peptides nor the incorporation of such peptides into liposomes, let alone for the purpose of promoting controlled liposome destabilization, has previously been described.

Vogel et al. and Subbaro et al. both covalently linked peptides to PEs; however, these peptide-lipids are not described therein as being cleavable by cell-secreted peptidases. Rather, the peptide-modified lipids of these documents are pH sensitive, adopting an alpha-helical conformation in low pH endosomal environments. Kirpotin et al. modified distearoyl phosphatidylcholine ("DSPE") by the attachment thereto of methoxypoly(ethylene glycol) ("mPEG") to DSPE on the amino group; liposomes containing mPEG-modified DSPE were stable in solution until thiolytic cleavage and removal of the mPEG moiety. Kirpotin does not describe the peptide-based modification of PEs, let alone with peptidase-cleavable peptides.

SUMMARY OF THE INVENTION

This invention provides a means of delivering and localizing the contents of liposomes to the vicinity of cells in a controlled manner, by conjugating certain peptides to phosphatidylethanolamines, and then incorporating these conjugated lipids into liposomes. The resulting liposomes are stable so long as the peptide remains conjugated to the lipid. However, once the peptide portion of the conjugate is cleaved from the lipid, by the action of cell-secreted peptidases, the liposomes tend to destabilize, so as to release their contents in the vicinity of, or into, the secreting cells. Delivery of the liposomes' contents is thus targeted to the peptidase-secreting cells.

Peptide-lipid conjugates of this invention have the formula:

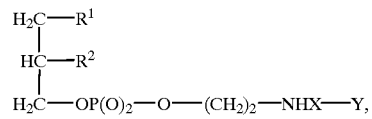

wherein: each of $R^1$ and $R^2$ is an acyl chain, X is a single bond or an acyl chain, and Y is a peptidase-cleavable peptide. The acyl chains are preferably oleic acid chains, X is preferably a single bond, and the peptide preferably contains the amino acid sequence Ala-Ala-Pro-Val [SEQ ID:1], more preferably, N-methoxysuccinyl-Ala-Ala-Pro-Val [SEQ ID NO:2]. Accordingly, the peptide-lipid conjugate preferably has the formula:

[SEQ ID NO:17]

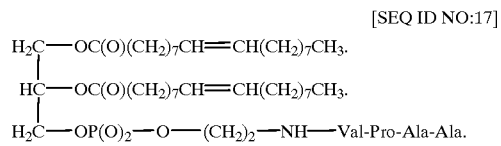

The liposomes' lipid component can be entirely composed of the peptide-lipid conjugate, or can comprise one or more additional lipids. Such additional lipids include, without limitation, any of the types of lipids, e.g., phospholipids, glycolipids and sterols, which may be used in the preparation of liposomes. Most preferably, the liposome of this invention comprises a peptide-lipid conjugate and the positively charged synthetic lipid 1-N,N-dimethylamino dioleoyl propane (DODAP).

Controlled delivery with the liposomes of this invention can be used to deliver the liposomal drugs in vitro or in vivo, for example, in the treatment of mammals afflicted with various diseases, disorders or conditions, e.g., cancers, amenable to treatment with the bioactive agent associated with the liposome.

BRIEF DESCRIPTION OF THE DRAWINGS

FIG. 2. TLC determination of protease mediated cleavage of N-Ac-AA-DOPE. N-Ac-AA-DOPE SUVs were incubated with elastase or proteinase K (1 mg enzyme/100 nmol lipid/0.1 ml buffer) overnight at 37° C. (results of elastase-mediated cleavage are depicted in FIG. 2A, and results of proteinase K-mediated cleavage are depicted in FIG. 2B). Lipid was collected and separated by TLC. Lipid spots were developed as described hereinbelow. Lane 1, N-Ac-AA-DOPE without enzyme; lane 2, N-Ac-M-DOPE with enzyme treatment; lane 3, DOPE from stock solution.

FIG. 3. Proteinase K mediated cleavage of N-Ac-M-DOPE. DOTAP/N-Ac-AA-DOPE (1:1) SUVs were incubated with or without elastase, proteinase K, or heat inactivated proteinase K (95° C., 1 hour) at a 1 mg protease/100 nmol/0.1 ml buffer lipid concentration overnight at 37° C. Lipid was collected and analyzed by HPLC. The N-Ac-AA-DOPE peak was quantitated and the amount of cleavage was calculated as a percentage of the starting lipid.

FIG. 4. Determination of optimal liposomal composition. Liposomes were prepared in given molar ratios of DOTAP, N-Ac-AA-DOPE, PE. 1 mol % N-NBD-PE and N-Rho-PE fluorescent probes were included in all preparations. Liposomes were mixed with unlabeled PE/PS or PC/PS (80/20 mol %; 1:10 effector:acceptor ratio; 60 uM total lipid) or $2 \times 10^8$ RBC ghosts at 37° C. for 1 hour. Lipid mixing was calculated as the percentage of N-NBD-PE FDQ relative to maximal FDQ, as determined by detergent addition. Binding of liposomes to RBC ghosts was quantitated after washing cells with buffer, by calculating the amount of N-Rho-PE fluorescence associated with the cell pellet relative to the total input fluorescence (results of mixing liposomes with unlabeled PE/PS or PC/PS are depicted in FIG. 4A, and results of mixing liposomes with RBC ghosts are depicted in FIG. 4B).

DETAILED DESCRIPTION OF THE INVENTION

Figure 1:
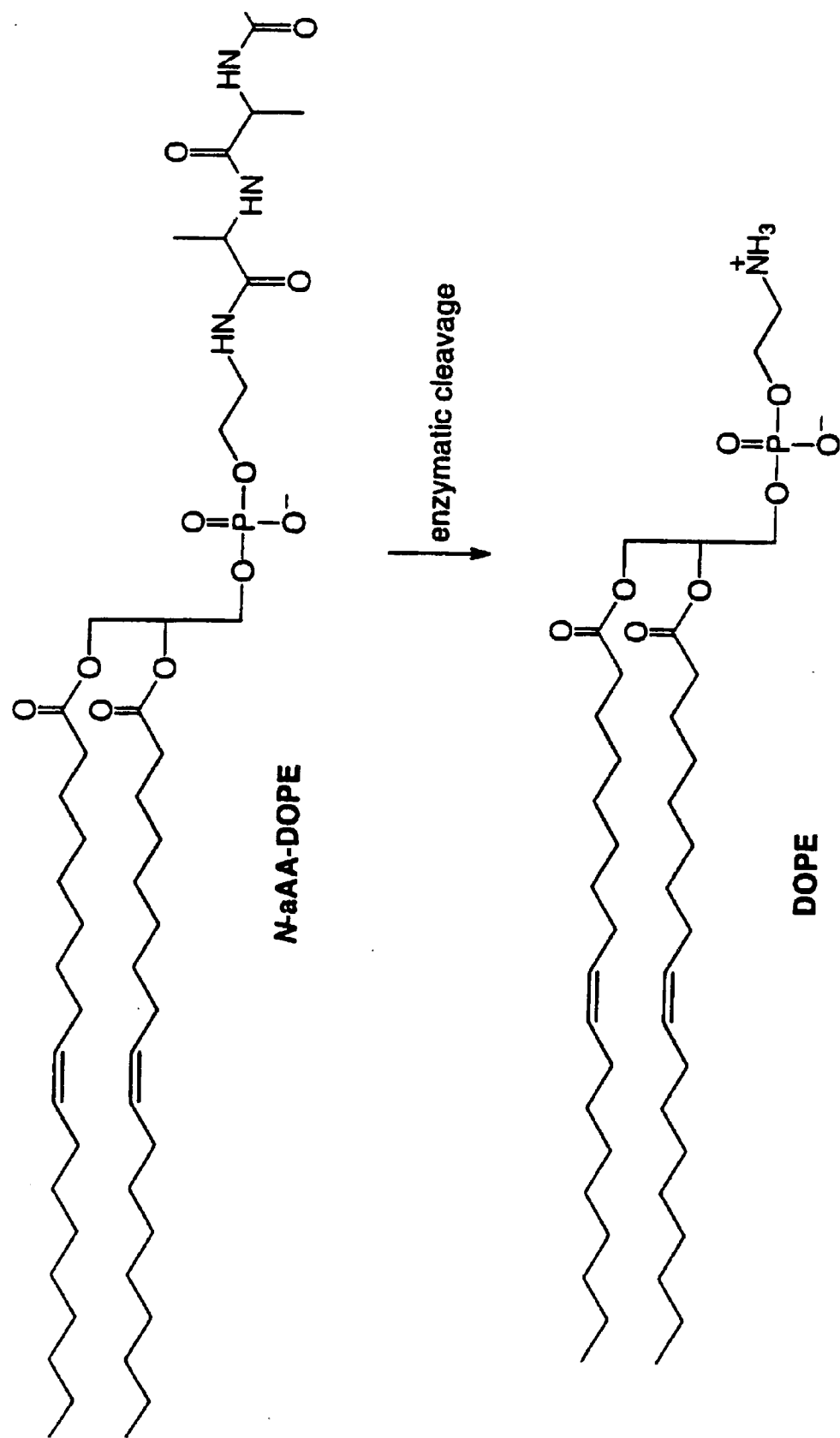
FIG. 1. Structure of N-Ac-M-DOPE and postulated scheme of conversion to DOPE by enzymatic cleavage.

This invention provides a peptide-lipid conjugate having the following formula:

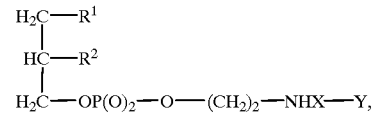

wherein: each of $R^1$ and $R^2$ is independently a group having the formula $-OC(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$ and X is a linker moiety selected from the group consisting of a single bond and an acyl chain having the formula —OC(O)(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$.

n1 is equal to zero or an integer of from 1 to 22, n3 is equal to zero or an integer of from 1 to 19, n5 is equal to zero or an integer of from 1 to 16, n7 is equal to zero or an integer of from zero to 13 and n9 is equal to zero or an integer of from 1 to 10; and, each of n2, n4, n6 and 8 is independently zero or 1. For R$^1$ and R$^2$ the sum of n1+2n2+n3+2n4+n5+2n6+n7+2n8+n9 is equal to an integer of from 10 to 22.

X is preferably a single bond; however, when X is other than a single bond, the sum of n1+2n2+n3+2n4+n5+2n6+n7+2n8+n9 for X is equal to an integer of from 1 to 22. X is then preferably saturated, most preferably —C(O)(CH$_2$)$_{11}$—.

Preferably, at least one of R$^1$ and R$^2$ contains at least one double bond, and the peptide-lipid conjugate is thus partially or completely unsaturated. More preferably, both of R$^1$ and R$^2$ contain one double bond, and the conjugate is thus completely unsaturated. Most preferably, presently, both R$^1$ and R$^2$ are —OC(O)(CH$_2$)$_7$(CH=CH)(CH$_2$)$_7$CH$_3$, i.e., the peptide-lipid conjugate is a dioleoyl phosphatidylethanolamine ("DOPE")-based conjugate. However, each of R$^1$ and R$^2$ can also be saturated or unsaturated acyl chains that include, without limitation: —OC(O)(CH$_2$)$_{14}$CH$_3$, —OC(O)(CH$_2$)$_{16}$CH$_3$, —OC(O)(CH$_2$)$_{18}$CH$_3$ or —OC(O)(CH$_2$)$_8$(CH=CH)(CH$_2$)$_8$CH$_3$.

Y is an "enzyme-cleavable peptide," which is a peptide comprising an amino acid sequence that is recognized by a peptidase expressed by a mammalian cell and found in surrounding tissue, or produced by a microbe capable of establishing an infection in a mammal. Enzyme-cleavable peptides can, but are not required to, contain one or more amino acids in addition to the amino acid recognition sequence; additional amino acids can be added to the amino terminal, carboxy terminal, or both the amino and carboxy terminal ends of the recognition sequence. Means of adding amino acids to an amino acid sequence, e.g., in an automated peptide synthesizer, as well as means of detecting cleavage of a peptide by a peptidase, e.g., by chromatographic analysis for the amino acid products of such cleavage, are well known to ordinarily skilled artisans given the teachings of this invention.

Enzyme-cleavable peptides, typically from about 2 to 20 amino acids in length, are of sufficient length to project above the surfaces of lipid-based carriers into which they have been incorporated. Such peptides are well known to ordinarily skilled artisans given the teachings of this invention and include, for example and without limitation, the amino acid sequences: Ala-Ala-, Ala-Ala-Pro-Val [SEQ ID NO:1], Ala-Ala-Met-, Ala-Ala-Pro-Phe- [SEQ ID NO:3], Ala-Ala-Pro-Met- [SEQ ID NO:4], Ala-Ala-Arg, Ser-Ala-Ala-Arg- [SEQ ID NO:5], Ser-Ser-Ala-Ala-Arg- [SEQ ID NO:6], Ser-S carboxyl sugar-Ala-Ala-Arg- [SEQ ID NO:7], Ala-Ala-Asp-, Ser-Ala-Ala-Asp- [SEQ ID NO:8], Ser-Ser-Ala-Ala-Asp- [SEQ ID NO:9], Arg-Pro-Lys-Pro-Leu-Ala-Nva- [SEQ ID NO:10], Ser-Arg-Pro-Lys-Pro-Leu-Ala-Nva- [SEQ ID NO:11], Ser-Ser-Arg-Pro-Lys-Pro-Leu-Ala-Nva [SEQ ID NO:12], Pro-Cha-Gly-Nva-His-Ala-Dpa-NH$_2$ [SEQ ID NO:13], Pro-Leu-Gly-Leu-Dpa-Ala-Arg-NH$_2$ [SEQ ID NO:14], Pro-Cha-Gly-Nva-, Pro-Leu-Gly-Leu [SEQ ID NO:15], Gly-Pro-Arg, Leu-Pro-Arg, Glu-Gly-Arg, and Gly-Pro-Gln-Gly-Ile- [SEQ ID NO:16]. Presently, the preferred peptides comprise the amino acid sequence Ala-Ala, more preferably, N-methoxysuccinyl-Ala-Ala-Pro-Val [SEQ ID NO:2].

Accordingly, the peptide-lipid conjugate of this invention most preferably has the formula:

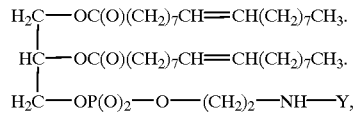

wherein the peptide comprises the amino acid sequence N-methoxysuccinyl-Ala-Ala-Pro-Val [SEQ ID NO:2].

Enzyme-cleavable peptides can be modified at their amino terminii, for example, so as to increase their hydrophilicity. Increased hydrophobicity enhances exposure of the peptides on the surfaces of lipid-based carriers into which the parent peptide-lipid conjugates have been incorporated. Polar groups suitable for attachment to peptides so as to increase their hydrophilicity are well known, and include, for example and without limitation: acetyl ("Ac"), 3-cyclohexylalanyl ("Cha"), acetyl-serine ("Ac-Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

Cell-secreted peptidases which recognize particular amino acid sequences are also well known to ordinarily skilled artisans given the teachings of this invention. Such peptidases include, for example and without limitation: matrix metalloproteinases, serine proteases, cysteine proteases, elastase, plasmin, plasminogen activator, stromelysin, human collagenases, cathepsins, lysozyme, granzymes, dipeptidyl peptidases, peptide hormone-inactivating enzymes, kininases, bacterial peptidases and viral proteases. Elastase, for example, is involved in tumor cell tissue remodeling; the breast cancer cell line MCF-7 has been shown to secrete elastase, the levels of which are inversely correlated to overall survival in breast cancer patients (Yamashita et al.). Moreover, the matrix metalloproteinase, stromelysin-3 ("ST3"), has been localized to the stromal area of tumor cells (Pei et al.); it specifically cleaves α$_1$ proteinase inhibitor between amino acids 350 and 351 (Ala-Met). Stromelysin-1 ("MMP-3") is also localized to areas of tissue remodeling, including sites of inflammation and tumor stroma (Nagase et al.).

The cDNA of human collagenase-3 or MMP-13, another metalloproteinase was isolated from a breast tumor library (Knäuper et al.); this enzyme cleaves peptides containing the amino acid sequences Pro-Cha-Gly-Nva-His- and Pro-Leu-Gly-Leu- [SEQ ID NO:15]. Furthermore, the 72 kDa gelatinase (MMP-2) is involved in regulating tumor cell invasiveness, and cleaves the amino acid sequence Gly-Pro-Gln-Gly-Ile- [SEQ ID NO:16] between the Gly and Ile residues (Aimes and Quigley; Liotta et al.). Human neutrophils also secrete collagenases at sites of inflammation such as MMP-8 (neutrophil collagenase) and MMP-9 (type IV collagenase, 92 kDa gelatinase) (Fosang et al.). Cathepsin G is also secreted from human neutrophils at sites of inflammation; its specificity is greatest for peptides containing the amino acid sequences Suc-Ala-Ala-Pro-Phe- [SEQ ID NO:18] or MeOSuc-Ala-Ala-Pro-Met- [SEQ ID NO:19] (Nakajima et al.). Other enzymes secreted by neutrophils at sites of inflammation include cathepsins B and D as well as lysozyme. Granzymes A and B are secreted by cytotoxic lymphocytes in the synovial fluid of rheumatoid arthritis patients (Froehlich et al.); granzyme A cleaves peptides comprising Gly-Arg- and Ala-Ala-Arg- most efficiently, while granzyme B cleaves peptides comprising the amino acid sequence Ala-Ala-Asp (Odake et al.).

Peptidases which hydrolyze enzyme-cleavable peptides also include the group of enzymes that inactivate peptide hormones, e.g., aminopeptidase P and angiotensin-converting enzyme, localized on the surface of endothelial cells. Aminopeptidase P cleaves the Arg-Pro bond in bradykinin, and is localized to lung endothelial cells (Prechel et al., 1995).

Peptide-lipid conjugates are prepared by any of a number of means for forming an amide bond between the amino group of a phosphatidylethanolamine and the carboxy terminus of an amino acid sequence. Such means include, without limitation, those described in Example 1, hereinbelow. Briefly, an enzyme-cleavable peptide containing an N-terminal blocking group is prepared as an anhydride; a phosphatidylethanolamine such as DOPE is then reacted with the anhydride in the presence of suitable reagents, such as triethylamine.

This invention also provides a liposome having a lipid component which comprises the peptide-lipid conjugate of the invention. "Liposomes" are self-assembling structures comprising one or more lipid bilayers, each of which surrounds an aqueous compartment and comprises two opposing monolayers of amphipathic lipid molecules. Amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium.

Liposomes of this invention can have a single lipid bilayer (unilamellar liposomes, "ULVs"), or multiple lipid bilayers (multilamellar liposomes, "MLVs"), and can be made by a variety of methods well known in the art. These methods include without limitation: Bangham's methods for making multilamellar liposomes (MLVs); Lenk's, Fountain's and Cullis' methods for making MLVs with substantially equal interlamellar solute distribution (see, for example, U.S. Pat. Nos. 4,522,803, 4,588,578, 5,030,453, 5,169,637 and 4,975, 282); and Papahadjopoulos et al.'s reverse-phase evaporation method (U.S. Pat. No. 4,235,871) for preparing oligo-lamellar liposomes. ULVs can be produced from MLVs by such methods as sonication or extrusion (U.S. Pat. No. 5,008,050 and U.S. Pat. No. 5,059,421). The liposome of this invention can be produced by the methods of any of these disclosures, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO89/008846), can also be used to regularize the size of liposomes, that is, to produce a population of liposomes having less size heterogeneity, and a more homogeneous, defined size distribution. The contents of these documents are incorporated herein by reference. Liposome sizes can also be determined by a number of techniques, such as quasi-elastic light scattering, and with equipment, e.g., Nicomp® particle sizers, well within the possession of ordinarily skilled artisans.

Liposomes of this invention can have lipid components entirely composed of a peptide-lipid conjugate. However, the liposomes preferably contain one or more additional lipids, including any of those lipids, such as phospholipids, glycolipids and sterols, typically used to prepare liposomes. Preferably, the additional lipid is a positively charged lipid, more preferably such a lipid selected from the group consisting of 1,2-bis(oleoyloxy)-3-(trimethylammonio) propane, (DOTAP) 1-N,N-dimethylamino dioleoyl propane (DODAP), 1-oleoyl-2-hydroxy-3-N,N-dimethylamino propane, 1,2-diacyl-3-N,N-dimethylamino propane and 1,2-didecanoyl-1-N,N,-dimethylamino propane, 3β[N-[(N', N'-dimethylamino)ethane]carbamoyl]cholesterol (DC-Chol), 1,2-dimyristooxypropyl-3-dimethylhydroxyethyl ammonium bromide (DMRIE) and 1,2-dioleooxypropyl-3-dimethylhydroxyethyl ammonium bromide (DORI).

Most preferably, presently, the positively charged lipid is DODAP. Positively charged lipids are incorporated into the liposomes, preferably in at most about equimolar concentration respective to the peptide-lipid conjugate, in order to adjust the net charge of the carrier. Increasing the positive charge on a lipid-based carrier enhances electrostatic interactions between the carrier and a biological membrane and hence, fusion between the carrier and the membrane.

The additional lipid can also include one or more phospholipids, such as a phosphatidylcholine ("PC"), which are generally added to lipid carriers to serve as structural stabilizers, or a phosphatidylethanolamine ("PE"). The PE may be selected from the group consisting of trans-esterified phosphatidylethanolamine (tPE), dipalmitoyl phosphatidylethanolamine (DPPE), palmitoyloleoyl phosphatidylethanolamine (POPE) and DOPE; such additional PE's, can be fusogenic because of the relatively unhydrated state of their headgroups.

Alternatively, the PE is a PE to the headgroup of which is attached a moiety selected from the group consisting of dicarboxylic acids, polyethylene glycols, polyalkyl ethers and gangliosides. Such modified PEs, also known as "headgroup-modified lipids," can inhibit the binding of serum proteins to lipid carriers such that the pharmacokinetic behavior of the carriers in the circulatory systems of animals is altered (see, e.g., Blume et al.; Gabizon et al.; Park et al.; Woodle et al.; and, Allen et al., the contents of which are incorporated herein by reference). The amount of the headgroup-modified lipid incorporated into the liposomes depends upon a number of factors well known to the ordinarily skilled artisan, or within his purview to determine without undue experimentation. These include, but are not limited to: the type of lipid and the type of headgroup modification; the type and size of the liposome; and the intended therapeutic use of the formulation. The concentration of the headgroup-modified lipid in the liposome is generally sufficient to prolong the liposome's circulatory half-life in an animal, but is not so great as induce unwanted side effects in the animal, and is typically at least about five mole percent of the lipid present in the liposome. Preferred headgroup-derivatized lipids include phosphatidylethanolamine-dicarboxylic acids ("PE-DCAs") and PEGylated lipids (for a description of which, see Woodle et al. and Allen et al.).

The liposome of this invention can comprise a "targeting moiety," i.e., a moiety that can be attached to a liposome and which can then direct the liposome to a specific site within the body of a mammal. Such directed delivery is generally believed to occur as a result of the recognition by the targeting moiety of a compound on the surface of the cells being targeted. Typical targeting moieties include, without limitation, antibodies, cell receptor ligands, lectins and the like. Targeting moieties can be attached to liposomes by any of the means generally accepted in the art for the covalent or noncovalent attachment of such moieties to liposomes. Such means include, for example and without limitation, those described in the following documents, the contents of which are incorporated herein by reference: U.S. Pat. No. 5,399,331 describes the coupling of proteins to liposomes through use of a crosslinking agent having at least one maleimido group and an amine reactive function; U.S. Pat. Nos. 4,885,172, 5,059,421 and 5,171,578 link proteins to liposomes through use of the glycoprotein streptavidin; Sato and Sunamoto describe the coating of targeted liposomes with polysaccharides.

The liposomes of this invention can comprise one or more "bioactive agents," which are compounds or compositions of matter having biological, including therapeutic or diagnostic, activity in animals. Bioactive agents which may be associated with the liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; nucleic acid sequences such as messenger RNA, cDNA, genomic DNA and plasmids; bioactive lipids such as ether lipids and ceramides; and the like. Preferred bioactive agents are selected from the group consisting of nucleic acid sequences, antimicrobial agents, anticancer agents and anti-inflammatory agents.

Preferably, the liposome has a lipid component which comprises a positively charged lipid and a peptide-lipid conjugate having the formula:

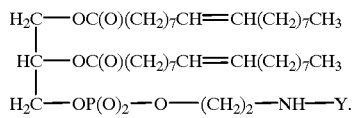

More preferably, the peptide comprises the sequence N-methoxy-succinyl-Ala-Ala-Pro-Val [SEQ ID NO:2] and the positively charged lipid is DODAP. Most preferably, presently, the lipid component comprises DODAP and the peptide-lipid conjugate in a respective molar ratio of about 50:50.

Further provided herein is a composition comprising the liposome and a "pharmaceutically acceptable carrier," which is a medium generally acceptable for use in connection with the administration of liposomes to mammals, including humans. Pharmaceutically acceptable carriers are formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Still further provided is a method of delivering the contents of a liposome to a cell which comprises contacting the cell with the liposome of this invention in the presence of a protease capable of cleaving the peptide-lipid conjugate. Delivery can occur in vitro, such as for diagnostic purposes or for ex vivo delivery of a therapeutic agent or nucleic acid to bone marrow cells. In vitro contact of a biological membrane with a lipid-based carrier involves adding the carrier-containing composition of this invention to cultures of protease-secreting cells, including various tumor cell lines such as the MCF-7 line, or adding an endogenous protease to the culture medium containing the membranes and the carriers.

Alternatively, the contacting can be in vivo, in which case the cells are preferably mammalian, a pharmaceutically acceptable carrier is used and the liposomes preferably comprise a targeting moiety. In vivo administration involves administering the compositions of this invention to the mammal by any of the means, e.g., by intravenous administration, generally accepted in the art for administering pharmaceutical compositions to mammals. The carriers will then circulate in the mammals, and will become fusogenic in the presence of peptidase concentrations sufficient to cleave the carriers' peptide-lipid conjugates; as described hereinabove, such peptidases are found in mammals at, for example, sites of inflammation, microbial infection and tumors. Moreover, incorporation of headgroup-modified lipids into lipid-based carriers increases the amount of time the carriers remain in circulation, and hence the proportion of the administered carrier reaching the intended site of action within the mammal. Furthermore, tumors generally have a higher degree of vasculature than does surrounding tissue, and these blood vessels are typically more permeable to structures such as lipid-based carriers. Accordingly, the carriers accumulate in tumors, thus further enhancing the proportion of administered carrier reaching the intended site of therapeutic action. Fusion in vivo can be to the cells secreting the protease as well as to nearby cells in the surrounding tissue.

In vivo liposomal bioactive agent delivery according to the practice of this invention can deliver therapeutically or diagnostically effective amounts of therapeutic or diagnostic agents into the cells of a mammal afflicted with a disease, disorder or condition amenable to diagnosis or treatment with the agent. Hence, such delivery can be used to diagnose or treat the mammal for the disease, disorder or condition.

The method of this invention can also be used to treat mammals afflicted with inflammatory disorders, by administering to the mammal a liposome containing an anti-inflammation effective amount of an anti-inflammatory agent. Treatable inflammatory disorders include, without limitation, arthritic disorders, autoimmune disorders, atherosclerotic plaque, acute respiratory distress syndrome, inflammatory bowel syndrome, acute nephritis or gout; suitable anti-inflammatory agents include, without limitation, nonsteroidal anti-inflammatory agents, glucocorticoids, bioactive lipids such as ceramides and ether lipids, and prostaglandins. Peptidases known to be present at sites of inflammation include, without limitation: elastase, which recognizes Ala-Ala- and cleaves peptides such as Ala-Ala-, Ala-Ala-Ala-, Ala-Ala-Pro-Val [SEQ ID NO:1], Ala-Ala-Pro-Met [SEQ ID NO:4] and Ala-Ala-Pro-Ala [SEQ ID NO:22]; stromelysin-1, which recognizes peptides comprising the amino acid sequence Arg-Pro-Lys-Pro-Leu-Ala-Nva- [SEQ ID NO:10], such as Ac-Arg-Pro-Lys-Pro-Leu-Ala-Nva [SEQ ID NO:23], MeOSucArg-Pro-Lys-Pro-Leu-Ala-Nva- [SEQ ID NO:24], carboxy sugar-Arg-Pro-Lys-Pro-Leu-Ala-Nva- [SEQ ID NO:25], Suc-Arg-Pro-Lys-Pro-Leu-Ala-Nva- [SEQ ID NO:26], Ser-Arg-Pro-Lys-Pro-Leu-Ala-Nva- [SEQ ID NO:11], Ac-Ser-Arg-Pro-Lys-Pro-Leu-Ala-Nva- [SEQ ID NO:27], MeOSuc-Ser-Arg-Pro-Lys-Pro-Leu-Ala-Nva- [SEQ ID NO:28], Ser-Ser-Arg-Pro-Lys-Pro-Leu-Ala-Nva- [SEQ ID NO:27], Ac-Ser-Ser-Arg-Pro-Lys-Pro-Leu-Ala-Nva- [SEQ ID NO;29]and MeOSuc-Ser-Ser-Arg-Pro-Lys-Pro-Leu-Ala-Nva [SEQ ID NO:30], and which cleaves the peptides at the Ala-Nva bond; and, cathepsin G, which is secreted by human neutrophils secreted at the site of inflammation, and cleaves peptides such as Suc-Ala-Ala-Pro-Phe- [SEQ ID NO:18], carboxy sugar-Ala-Ala-Pro-Phe- [SEQ ID NO:31], MeOSuc-Ala-Ala-Pro-Met- [SEQ ID NO:19], Suc-Ala-Ala-Pro-Met [SEQ ID NO;32], and carboxy sugar-Ala-Ala-Pro-Met- [SEQ ID NO;33].

Moreover, peptide substrates for the enzymes granzyme A and granzyme B, secreted by cytotoxic lymphocytes in the synovial fluid of rheumatoid arthritis patients, include, without limitation: Ac-Ala-Ala-Arg-, MeOSuc-Ala-Ala-Arg-, Ala-Ala-Arg-, Ser-Ala-Ala-Arg- [SEQ ID NO:5], Ac-Ser-Ala-Ala-Arg- [SEQ ID NO:34], MeOSuc-Ser-Ala-Ala-Arg- [SEQ ID NO:35], Ser-Ser-Ala-Ala-Arg- [SEQ ID NO:6], Ac-Ser-Ser-Ala-Ala-Arg- [SEQ ID NO:36], MeOSuc-Ser-Ser-Ala-Ala-Arg- [SEQ ID NO:37] and carboxyl sugar-Ala-Ala-Arg-, etc. Ac-Ala-Ala-Asp-, MeOSuc-Ala-Ala-Asp-, Ala-Ala-Asp-, Ser-Ala-Ala-Asp- [SEQ ID NO:8], Ac-Ser-Ala-Ala-Asp- [SEQ ID NO:38], MeOSuc-Ser-Ala-Ala-Asp- [SEQ ID NO:39], Ser-Ser-Ala-Ala-Asp- [SEQ ID NO:9], Ac-Ser-Ser-Ala-Ala-Asp- [SEQ ID NO:40], MeOSuc-Ser-Ser-Ala-Ala-Asp- [SEQ ID NO:41], and carboxyl sugar-Ala-Ala-Asp-. Dipeptidylaminopeptidase IV (DAP IV, EC 3.4.14.5), a member of the dipeptidyl peptidase enzyme family, is found in increased concentrations on pig aorta smooth muscle cells (Palmieri et al.). Vessel wall damage, e.g., after angioplasty or during other inflammatory states exposes the peptidase. For instance, inflammatory edema is associated with breach of the endothelial lining and exposure of smooth muscle cells. Appropriate substrates could be used for liposomal delivery to these sites.

The method of this invention can also be used to treat mammals afflicted with cancers, by administering to the mammals a liposome containing an anticancer effective amount of an anticancer agent. Treatable cancers include brain, breast, colon, lung, ovarian, prostate and stomach cancers, as well as sarcomas, carcinomas, leukemias, lymphomas and melanomas; suitable anticancer agents include, without limitation, anthracycline antibiotics, bioactive lipids such as ceramides and ether lipids, taxanes and vinca alkaloids. Peptidases known to be present in the vicinity of tumors include, for example and without limitation: elastase, which cleaves peptides containing the amino acid sequence Ala-Ala-, Ala-Ala-Pro-Val [SEQID NO:1] (Nakajima et al., Castillo et al.); stromelysin-3, which cleaves peptides containing the amino acid sequence Ala-Met; stromelysin-1, which cleaves peptides containing the amino acid sequence Ala-Nva-; human collagenase-3, which cleaves peptides such as MeOSuc-Pro-Cha-Gly-Nva-, Suc-Pro-Cha-Gly-Nva-, Pro-Cha-Gly-Nva-, Pro-Leu-Gly-Leu- [SEQ ID NO:15], MeOSuc-Pro-Leu-Gly-Leu- [SEQ ID NO:20] and Suc-Pro-Leu-Gly-Leu- [SEQ ID NO:21]; and, the 72-kD gelatinase, which cleaves peptides containing the amino acid sequence Gly-Pro-Gln-Gly-Ile- [SEQ ID NO:16] (see Pei et al.; Knäuper et al.; Boyd; Unden et al.; and, Kossakowska et al.) and urokinase plasminogen activator, which cleaves Glu-Gly-Arg and Ac-Lys (Wohl et al.; Johnson et al.; Petkov et al.; Ascenzi et al.), and cathepsin B, which cleaves Arg-Arg Knight; Barrett & Kirschke; Kirschke et al.).

Moreover, specific peptidases are also found in neuronal tissue (e.g. O'Leary and O'Connor), suggesting that the liposomes may be designed to treat several neuropathies. Specific aminopeptidases are produced on the membranes of the placental tissue and later secreted suggesting primarily localization of this activity in the placenta (Rogi et al.). Several kininases are localized to the kidney. For example renin is found in the zona glomerulosa and/or adrenal medulla (Berka et al.). Certain peptidases have even been identified in skeletal muscle (Ward et al.).

Observation of strong activity of an alanylaminopeptidase in the stroma of basal cell carcinoma and DAP IV in the tumor cells themselves (Moehrle et al.) suggest an alanyl-phospholipid or appropriate dipeptides as possible triggers for liposomal fusion with tumor cells.

The method of this invention can also be used to treat mammals afflicted with microbial infections, by administering to the mammals a liposome containing an anti-infection effective amount of an anti-infective agent, such as the various antibiotics. A number of specific peptidases are associated with certain bacteria and may be utilized to deliver liposomal contents to sites of infection (e.g. Spratt et al.). Human immunodeficiency viruses have proteases with particular specificities (e.g. Hoog et al.) that may be expressed in or near infected cells and may be utilized to target fusogenic liposomes for therapy.

The contents of the above-cited documents, with their descriptions of secreted enzymes and their target peptides, are incorporated herein by reference.

Liposomal drug delivery according to the practice of this invention can direct the liposomes contents to the vicinity of the target cells. It can also deliver the contents directly into cells, by way of fusion between the liposomes and the cells. "Fusion" of a liposome to a cell involves both binding of the liposome to the cell, as well as mixing of liposomal and cell membrane lipids. Binding and lipid mixing can be assessed by a number of means well known to ordinarily skilled artisans given the teachings of this invention including, for example, those described hereinbelow.

Briefly, liposomes are labeled by incorporation therein of a fluorescent marker and mixed with erythrocyte ghosts, prepared as described ihereinbelow. Erythrocyte ghosts are incapable of endocytosis, and hence, any transference of fluorescence between the liposome and ghosts must be due to fusion. Measurement of erythrocyte ghost fluorescence is thus a measure of the fusion of liposome to the ghosts. Peptidase-mediated cleavage of a peptide-lipid conjugate herein converts a nonfusogenic liposome into a fusogenic liposome. Moreover, the liposome can contain one or more additional fusogenic lipids, including PE's such as DOPE and synthetic lipids such as DOTAP and DODAP. Such lipids promote fusion of their parent liposomes to adjacent lipidic membranes, because of the nonbilayer structures adopted by the lipids in aqueous environments.

However, the peptide-lipid conjugate can also contain a "blocking" group, e.g., a carboxy sugar such as lactobionic acid or N-acetyl neuraminic acid, or a polymeric compound such as a small polyethylene glycol derivative, a polyhydroxyl polymer or a number of other amino acids in the range of 1–10 of a composition containing hydrophilic side chains such as serine or threonine. This blocking group is attached to the N-terminus of the peptide, and inhibits or blocks the liposome and lipidic membrane from approaching closely enough for fusion between the two to occur. Cleavage of the peptide by a protease removes this N-terminal blocking group from the peptide, and hence, allows for fusion between the liposome and the lipidic membrane. Peptidase-mediated cleavage thus, by cleaving the peptide portion of the peptide-lipid conjugate, results in the generation of a fusogenic lipid.

This invention will be better understood in light of the following Examples. However, those of ordinary skill in the art will readily understand that the examples are merely illustrative of the invention as defined in the claims which follow thereafter.

EXAMPLES

Example 1

A) Chemical Synthesis of N-Ac-Ala-Ala-DOPE

N-acetyl-alanyl-alanyl-dioleoyl phosphatidylethanolamine ("N-Ac-Ala-Ala-DOPE") was synthesized by first preparing an anhydride form of the peptide from N-acetyl-ala-ala-OH, or other suitably blocked carboxyl-terminating peptides; the starting reagent was incubated with N,N-dicyclohexyl carbodiimide (DCC) in the presence of chloroform for a few hours at room temperature. The end-product anhydride is soluble in chloroform, whereas a reaction by-product (dicyclohexyl urea) is not; therefore the anhydride is separated from the undesired by-product by collecting the chloroform and discarding the precipitate.

DOPE is added to the anhydride in the presence of triethylamine to catalyze the N-acylation reaction; the mixture is incubated overnight at room temperature. The reaction mixture is applied to a preparative thin layer chromatography (TLC) plate to purify N-acetyl-ala-ala-DOPE, the solvent system being chloroform/methanol/water (65/25/4). The lipid band is identified by spraying the plate with water, after which the band is scraped and solubilized in chloroform/methanol (2/1). Lipid is stored under nitrogen at −70 C.

B) Chemical Synthesis of 1,2-Dioleoyl-sn-glycero-3-phosphoethanolamido-val-pro-ala-ala-sucOMe (MeOSuc-Ala-Ala-Pro-Val-DOPE) [SEQ ID NO:42]:

i) p-Nitrophenyl-val-pro-ala-ala-sucOMe ester: To a solution of H-val-pro-ala-ala-sucOMe peptide (540 mg, 1.15 mmol), were added 142 mg (1.38 mmol) of p-nitrophenol, 175 mg (1.38 mmol) of 1,3-dicyclohexylcarbodiimide and catalytic amount (few crystals) of 4-dimethylaminopyridine in 10 ml of dry chloroform. The reaction mixture was stirred overnight under nitrogen atmosphere at room temperature. At this point TLC analysis showed that the reaction had gone to completion. The precipitate (DCU) from the reaction mixture was filtered using a G-2 funnel and the filtrate concentrated under reduced pressure. The residual material used in the next step without purification; $R_f$ 0.43 ($CHCl_3$:MeOH 9:1 v/v).

ii) 1,2-Dioleoyl-sn-glycero-3-phosphoethanolamido-val-pro-ala-ala-sucOMe [SEQ ID NO:42]: To a solution of p-nitrophenyl ester of val-pro-ala-ala-sucOMe (600 mg, 1.01 mmol), were added 604 mg (0.81 mmol) of 1,2-dioleoyl-sn-glycero-3-phosphoethanolamine and 82 mg (113 mL, 0.81 mmol) of triethylamine in 20 ml of mixture of solvents chloroform:tetrahydrofuran (1:4 v/v). The reaction mixture was stirred under nitrogen atmosphere at room temperature overnight. TLC analysis showed that the reaction had gone to completion. The reaction mixture was concentrated under reduced pressure and passed through activated TMD-8 ion exchange resin in $THF:H_2O$ (9:1 v/v).

The phosphorus positive fractions were pooled and concentrated to get the residual product. The residual material was purified by silica gel column chromatography (column was washed with 5% methanol in chloroform, then eluted with $CHCl_3$:MeOH:$NH_4OH$ 65:25:4 v/v/v), giving 915 mg (95% yield on the basis of DOPE), which on lyophilization gave a white solid: Rf 0.76 ($CHCl_3$:MeOH:$NH_4OH$ 65:25:4 v/v/v) and Rf 0.43 ($CHCl_3$:MeOH:$H_2O$ 65:25:4 v/v/v).

The lipopeptide molecule gave a positive test for molybdenum reagent and a negative test for ninhydrin reagent. The lipopeptide molecule identity was determined by TLC in two solvent systems: ((i) $CHCl_3$:MeOH:NH4OH 65:25:4 v/v/v and (ii) $CHCl_3$:MeOH:$H_2O$ 65:25:4 v/v/v). In both solvent systems the lipopeptide gave a single spot and it is >99% pure. The lipopeptide was characterized by NMR and FAB mass analysis. $^1$H-NMR ($CDCl_3$) some characteristic signals are shown here: d 0.87 (t, 3H, J=7.15 Hz), 1.27 (40H), 1.56 (4H), 2.0 (8H), 2.23 (t, 4H, J=7.15 Hz), 5.17 (1H), 5.32 (4H, J=3.12 Hz). $^{31}$P-NMR Spectrum gave single signal. FAB ($MH^+$) calcd for $C_{62}H_{109}N_5O_{15}P$ 1195.55, found 1196.8 ($MH^+$) and 1234.9 ($MK^+$).

Example 2

Cleavage of N-Ac-ala-ala-DOPE

Cleavage of N-Ac-ala-ala-DOPE to DOPE by elastase was monitored by thin layer chromatography (TLC). 100–200 nmol of N-Ac-M-DOPE SUVs were incubated with 1 mg enzyme in 0.1 ml overnight at 37° C. Lipid was extracted by organic phase separation [Bligh, et al., (1959)] twice. Collected lipid was dried under $N_2$ stream and exposed to vacuum for 4 hours-overnight. Samples were resuspended in chloroform and spotted onto TLC plates. TLC was run using chloroform/methanol/water (65:25:4), air dried, sprayed with molybdenate blue, and charred on a hot plate. Treatment of N-Ac-AA-DOPE liposomes with elastase generated a product corresponding to DOPE, whereas untreated N-Ac-M-DOPE showed no change (FIG. 2A). Therefore elastase recognized N-Ac-M-DOPE and cleaved the dipeptide to yield DOPE.

Several proteases were tested to determine whether an enzyme with similar substrate specificity could be used as a model for elastase mediated cleavage of N-Ac-AA-DOPE. Proteinase K is a serine protease that, similarly to elastase, can cleave at peptide bonds C-terminal to aliphatic residues. Upon incubation of N-Ac-AA-DOPE liposomes with proteinase K the peptide-lipid was cleaved and DOPE was generated (FIG. 2B).

The conversion of N-Ac-M-DOPE to DOPE was also monitored by $^{31}$P-NMR analysis. N-Ac-M-DOPE LUVs were prepared and treated with or without proteinase K (1.5 mg protein/100 nmol lipid) overnight at 37° C. Samples were mixed with buffer (10% deoxycholate, 100 mM EDTA, 20 mM Hepes) and deuterium oxide (Cambridge Isotope Laboratories, Woburn, Mass.) (1:4:2) and transferred to 5 mm NMR tubes. Samples were monitored at room temperature in a Bruker AC300 spectrometer operating at 121.5 MHz, with 110 ms 90° radio frequency pulse for proton decoupling and set to 2 sec interpulse delay to avoid signal saturation. Sweep width was set at 50 kHz. 1 Hz line broadening was applied to all spectra. N-Ac-AA-DOPE liposomes treated with proteinase K (1.5 mg protease/100 nmol lipid) resulted in the appearance of a peak 0.3 ppm upfield from N-Ac-AA-DOPE, corresponding with pure DOPE.

Elastase and proteinase K mediated cleavage of N-Ac-AA-DOPE was quantitated using liposomes composed of N-Ac-M-DOPE and DOTAP, a positively charged lipid. DOTAP was included to provide a counterbalancing positive charge, and was used as a standard by which different samples could be normalized and compared. After treatment with elastase or proteinase K the reduction in the amount of N-Ac-AA-DOPE was monitored by HPLC. Liposomes composed of DOTAP/N-Ac-M-DOPE (1:1) or DOTAP/N-Ac-AA-DOPE/PE (15/15/70 mol %) were incubated with enzyme under given conditions. Lipid was extracted by the Bligh-Dyer procedure twice.

Collected lipid was dried under $N_2$ stream and exposed to vacuum for 4 hours-overnight. Samples were resuspended in 100% ethanol and injected in 30 ul aliquots into Spherisorb silica columns (150×4.6 mm, 0.3 um, Keystone Scientific). HPLC was performed using a hexane:isopropanol:water:TFA mobile phase. Hexane and TFA were held constant at 37% and 0.2%, respectively. The N-Ac-M-DOPE peak was detected using a gradient of 59–55% isopropanol:4–8% water. Flow rate was 1.5 ml/min, column temperature was set at 45° C., and peaks were detected by a UV detector set at 205 nm. Lipid peaks were quantitated in comparison to standard curves generated by injecting 5–200 nmol of DOTAP or N-Ac-AA-DOPE and monitoring 205 nm signal. % cleavage was calculated by normalizing peaks to DOTAP, then determining the decrease in N-Ac-AA-DOPE peak size relative to starting amounts.

Both elastase and proteinase K cleaved N-Ac-M-DOPE to a similar extent (FIG. 3). To verify that the cleavage of N-Ac-AA-DOPE was due to proteinase K enzymatic activity, liposomes were treated with heat inactivated proteinase K. Proteinase K was inactivated by heating at 95° C. for 1 hour, after which the enzyme was incapable of cleaving the chromogenic substrate N-Ac-AAA-pNA. Treatment of DOTAP/N-Ac-AA-DOPE liposomes with heat inactivated proteinase K did not result in any cleavage of N-Ac-AA-DOPE (FIG. 3), indicating the requirement for active proteinase K. Since proteinase K has been shown to share substrate specificity with elastase and is considerably less costly than human leukocyte elastase, the majority of subsequent experiments were conducted with proteinase K.

Example 3

Cleavage of MeOSuc-Ala-Ala-Pro-Val-DOPE [SEQ ID NO:42] by human leukocyte elastase (HLE)

A) HLE dose titration

To determine if the peptide-lipid MeOSuc-Ala-Ala-Pro-Val-DOPE [SEQ ID NO:42] is also a suitable substrate for elastase mediated cleavage 50 nmol of MeoSuc-Ala-Ala-Pro-Val-DOPE [SEQ ID NO:42] liposomes (SUVs) were incubated with 0, 2.5, 5, 10, or 20 ug HLE (from Calbiochem; 20 units/mg protein; 1 unit=amount of enzyme that will hydrolyze 1.0 umol of MeO-suc-ala-ala-pro-val-pNA per min at 25 C, pH 8.0) overnight at 37 C in 50 ul volume of 10 mM TES/154 mM NaCl/0.1 mM EDTA, pH 7.4, containing 1.5 mM Ca and 1.5 mM Mg.

Lipid was extracted using the Bligh-Dyer technique (chloroform/methanol/water 2/1.7/1), dried under nitrogen, placed under high vacuum for ~3 hours. Samples were resuspended in 5 ul chloroform and spotted onto TLC plates. 20 ug of pure DOPE was also spotted for comparison purposes. TLC solvent system was chloroform/methanol/ammonium hydroxide (65/25/5). Plates were air dried, sprayed with molybdenate blue, then charred at 180 C.

B) Cleavage of MeOSuc-Ala-Ala-Pro-Val-DOPE [SEQ ID NO:42] by human neutrophil granule proteins Since elastase is produced by activated neutrophils the cleavage of MeOSuc-Ala-Ala-Pro-Val-DOPE [SEQ ID NO:42] by unpurified granule proteins was monitored to mimic more closely the in vivo situation. Neutrophils were obtained from human whole blood by standard procedures employing density centrifugation. Granules were isolated from these neutrophils by centrifugation following nitrogen cavitation of cells, again following established procedures. Protein concentration of neutrophil granules was determined after repeated freeze-thawing of granules to release proteases.

50 nmol MeOSuc-Ala-Ala-Pro-Val-DOPE [SEQ ID NO:42] liposomes (SUVs) were incubated with 0, 2.5, 5, 10, or 20 ug neutrophil granule proteins overnight at 37 C in 50 ul volume of 10 mM TES/154 mM NaCl/0.1 mM EDTA, pH 7.4, containing 1.5 mM Ca and 1.5 mM Mg. Samples were processed as described above. Results show that 2.5 $\mu$g of neutrophil granule proteins were sufficient to detect cleavage of MeOSuc-Ala-Ala-Pro-Val-DOPE [SEQ ID NO:42] to DOPE, suggesting that crude neutrophil granule proteins can convert the peptide-lipid to DOPE, and therefore liposomes containing this peptide-lipid can be activated to fuse under physiological conditions.

C) Kinetics of HLE mediated cleavage of MeOSuc-Ala-Ala-Pro-Val-DOPE [SEQ ID NO:42]

MeOSuc-Ala-Ala-Pro-Val-DOPE [SEQ ID NO:42] liposomes were incubated with 0 or 5 ug HLE for 1, 2, 4 hours, or overnight and processed as above. The peptide was cleaved by HLE in as little as 1 hour at 37 C, suggesting that the cleavage of MeOSuc-Ala-Ala-Pro-Val-DOPE [SEQ ID NO:42] occurs within a physiologically relevant time frame.

Figure 11A:
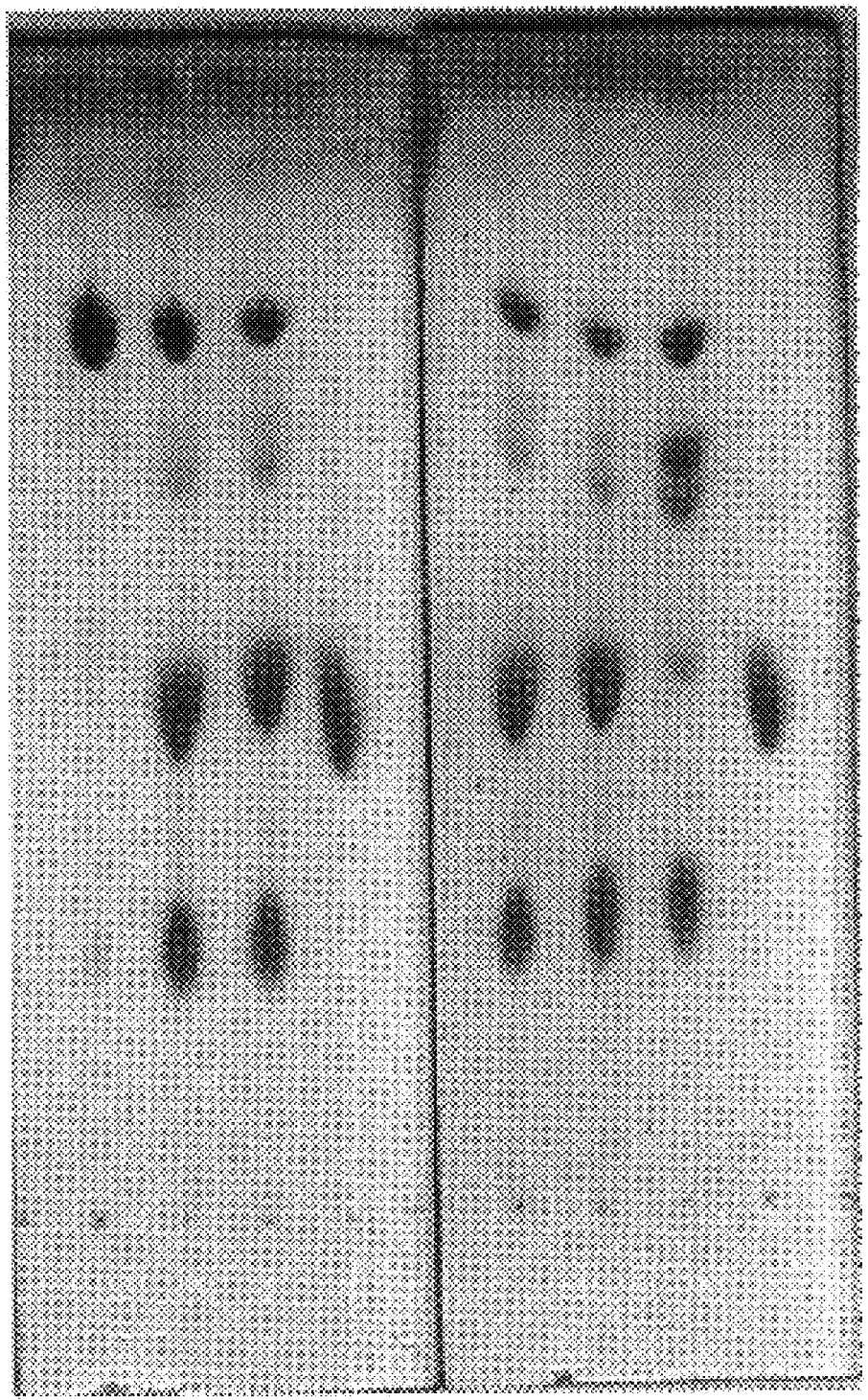
FIG. 11. TLC determination of the cleavage of MeO-suc-Ala-Ala-Pro-Val-DOPE [SEQ ID NO:42]. HLE dose titration: 1/ 0 ug HLE/100 nmol lipid; 2/ 5 ug HLE/100 nmol lipid; 3/ 10 ug HLE/100 nmol lipid; 4/ pure DOPE, 20 ug; 5/ 20 ug HLE/100 nmol lipid; 6/ 40 ug HLE/100 nmol lipid; 7/ 40 ug proteinase K/100 nmol lipid; 8/ pure DOPE, 20 ug; Cleavage of MeO-suc-AAPV-PE [SEQ ID NO:43] by human neutrophil granule proteins: 1/ w/o protease; 2/ 5 ug HLE/50 nmol lipid; 3/ 2.5 ug granule proteins/100 nmol lipid; 4/ pure DOPE, 20 ug; 5/ 5 ug granule proteins/100 nmol lipid; 6/ 10 ug granule proteins/100 nmol lipid; 7/ 20 ug granule proteins/100 nmol lipid; 8/ pure DOPE, 20 ug. Kinetics of HLE cleavage: 1/ w/o protease; 2/ 1 hour, 5 ug HLE/50 nmol lipi; 3/ 2 hours, 5 ug HLE/50 nmol lipid; 4/ pure DOPE, 20 ug; 5/ 4 hours, 5 ug HLE/50 nmol lipid; 6/ overnight, 5 ug HLE/50 nmol lipid; 7/ pure DOPE, 20 ug (FIG. 11A depicts results of HLE dose titration.
FIG. 11B depicts results of the cleavage of MeO-suc-AAPV-PE; and, FIG. 11C depicts results showing the kinetics of HLE cleavage).
Figure 11B:
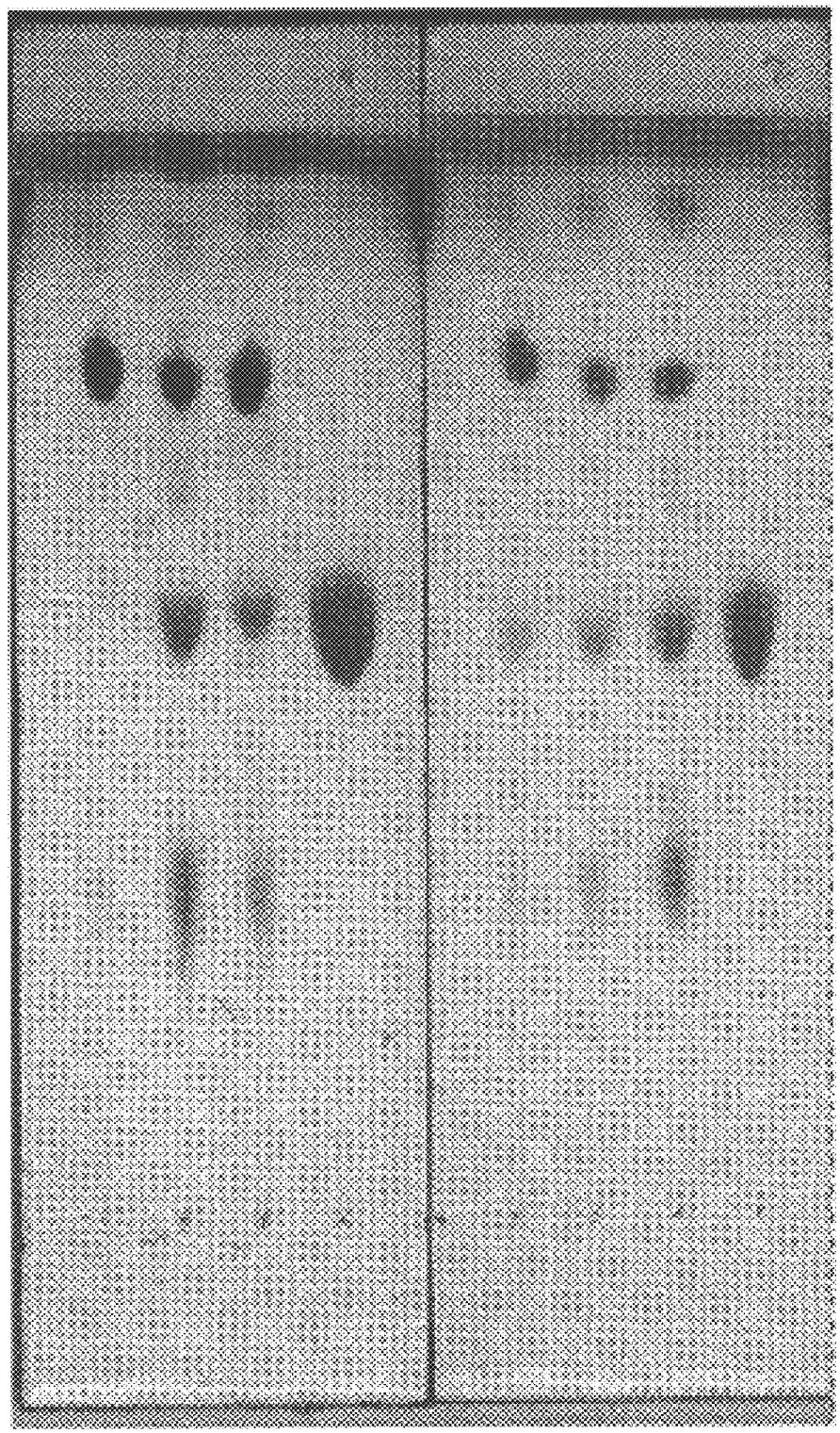
Figure 11C:
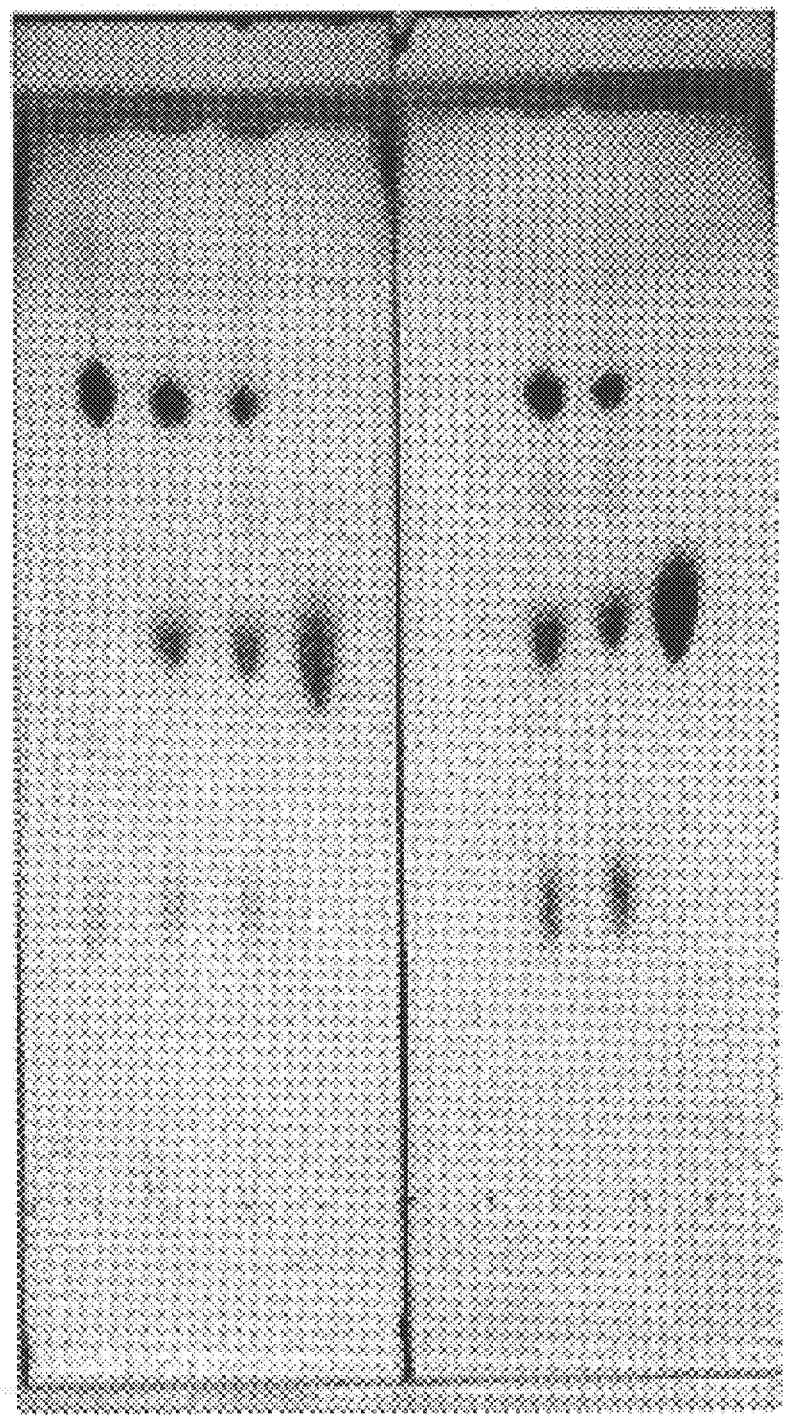

Results of these experiments are presented in FIG. 11.

Example 4

Liposome Preparation

NBD/Rh labeled or unlabeled large unilamellar vesicles (LUVs) were prepared as described before (Mayer et al.). Briefly, the lipid mixture in chloroform was dried under a nitrogen stream to a thin film, which was then left under vacuum overnight to remove residual solvent. The lipid film was hydrated with TES buffered saline (10 mM TES, 0.1 mM EDTA, 154 mM NaCl, pH 7.4). Brief vortexing was applied to ensure complete hydration. After ten cycles of freeze/thaw in liquid nitrogen/room temperature water bath, the sample was extruded ten times through 0.1 $\mu$m polycarbonate membrane filter (Poretics Corp., Livermore, Calif.). The liposomes were stored at 4° C. Multilamellar vesicles were prepared by hydrating the dried lipid film.

The phospholipid concentration of each liposome preparation was determined by phosphate assay (Bartlett). The approximately 0.1 $\mu$m size of the liposomes was confirmed on a Nicomp submicron particle sizer (Nicomp Instruments, Inc., Goleta, Calif.) using quasi-elastic light scattering.

Example 5

Preparation of Resealed and Unsealed Human Erythrocyte Ghosts

Resealed ghosts are referred to as erythrocyte ghosts unless otherwise specified, and were prepared as previously described (see Williamson et al.; Clague et al., the contents of which are incorporated herein by reference). Briefly, fresh human blood was washed several times with cold 10 mM TES buffered saline to remove plasma and white cells. Then 2 ml of washed erythrocytes (50% hematocrit) were pre-swelled in cold hypotonic solution containing 8 ml H$_2$O and 9.6 ml 10 mM TES buffered saline, and then pelleted at 850× g for 5 minutes. The pellet was resuspended in 40 ml cold lysis buffer (10 mM Tris, 0.1% BSA, 2 mM MgCl$_2$, and 0.1 mM EGTA) and incubated on ice for at least 2 minutes. After addition of 4.5 ml 10× resealing buffer (1.22 M NaCl, 30 mM KCl, 0.15 M Na$_2$HPO$_4$, 50 mM KH$_2$PO$_4$, and 2 mM MgCl$_2$), the sample was incubated at 37° C. for 40 minutes. The resealed ghosts were pelleted at 1750× g for 10 minutes and washed several times until no hemoglobin could be observed in the supernatant. The ghosts were stored at 4° C. and used within one week.

Example 6

Design of fusion-triggerable liposomes containing N-Ac-AA-DOPE

The threshold of fusogenicity was determined by preparing liposomes with increasing amounts of PE transesterified from egg PC. This PE was preferred over DOPE because of its higher H$_{II}$ transition temperature (~37° C. vs. 10° C., respectively), which aids in the preparation of stable liposomes yet does not inhibit fusion. DOTAP was chosen as the positively charged lipid. Fusion assays were performed for DOTAP/N-Ac-AA-DOPE/PE liposomes containing the fluorescent membrane probes N-NBD-PE and N-Rho-PE and inversely varying amounts of N-Ac-AA-DOPE and PE. These liposomes were monitored for lipid mixing with either unlabeled target liposomes or for lipid mixing and binding with RBC ghosts. Lipid mixing between NBD/Rh labeled liposomes and unlabeled ghosts was measured in 10 mM TES buffered saline by the NBD/Rh resonance energy transfer (RET) assay (Struck et al., the contents of which are incorporated herein by reference).

Liposomes were prepared with 1 mol % N-NBD-PE and 1 mol % N-Rho-PE, which results in quenching of the N-NBD-PE fluorescence signal. Membrane fusion results in probe diffusion and relief from self-quenching, which is monitored as an increase in N-NBD-PE fluorescence. Liposome-liposome lipid mixing was initiated by addition of 10 nmol of fluorescently labeled liposomes to 90 nmol unlabeled liposomes in microcentrifuge tubes containing 1 ml of TES/NaCl/EDTA buffer with 1.5 mM Ca$^{++}$/1.5 mM Mg$^{++}$. For fusion with cells 1×10$^8$ RBC ghosts were substituted for unlabeled liposomes. All samples were shaken in an Eppendorf Thermomixer (Brinkmann Instruments, Inc., Westbury, N.Y.), 700 rpm/min, during the 37° C. incubation for 30 min. N-NBD-PE fluorescence was monitored in a T-format PTI Alphascan spectrafluorometer (Princeton, N.J.) with a xenon short arc lamp using 450 nm excitation/ 530 nm emission wavelengths and 5 nm slitwidths. 450 nm band pass and 500 nm cutoff filters were utilized for excitation and emission light paths, respectively, to reduce stray light. Maximal fluorescence dequenching was determined by addition of 0.1% C12E8 detergent.

It became readily apparent that the threshold for fusogenicity depends upon the target in question. Liposomes composed of DOTAP and PE fused with both target liposomes and RBC ghosts. Inclusion of 10 mol % N-Ac-M-DOPE with a corresponding decrease in PE to 70 mol % generated liposomes that were still capable of fusing with PE/PS liposomes but not PC/PS liposomes (FIG. 4A). The requirements for membrane fusion with RBC ghosts appeared to be more stringent, with inclusion of 5 mol % N-Ac-AA-DOPE inhibiting both the lipid mixing and the binding significantly (FIG. 4B). Defining the different threshold of fusion for different targets creates a gradient of sensitivity for fusion that can be used to determine optimum conditions for activating N-Ac-AA-DOPE containing liposomes to fuse. As PE/PS liposomes appeared to be the most sensitive target, we focused on a composition of DOTAP/ N-Ac-AA-DOPE/PE liposomes that could be activated to fuse. The threshold of PE content appeared to be between 65–70 mol %. In order to create a liposome that is not initially highly positively charged, DOTAP and N-Ac-AA-DOPE were added in equivalent amounts to yield liposomes composed of DOTAP/N-Ac-AA-DOPE/PE in a 15/15/70 mol ratio.

Example 8

Activation of liposome-liposome lipid mixing by enzyme cleavage

Since elastase and proteinase K were capable of cleaving N-Ac-M-DOPE to DOPE (FIGS. 2, 3), both enzymes were tested for their ability to activate DOTAP/N-Ac-AA-DOPE/ PE (15/15/70 mol %) liposomes to fuse. These liposomes were treated overnight at 37° C. with elastase, or proteinase K, or without either enzyme, after which liposomes were incubated with PE/PS liposomes and lipid mixing monitored by relief of N-NBD-PE fluorescence quenching. Liposomes were incubated with protease at a 1 mg protease/100 nmol lipid/0.1 ml buffer ratio, unless otherwise stated. This concentration of proteinase K was found to have comparable activity, within an order of magnitude, with that of elastase in rheumatoid arthritis synovial fluid [Al-Haik, et al., (1984)]. Mixtures were incubated at 37° C. in microcentrifuge tubes with constant shaking in an Eppendorf Thermomixer, 700 rpm/min. Treated liposomes were then assayed for N-Ac-AA-DOPE cleavage by HPLC, as described above. For fusion experiments liposomes containing fluorescent membrane probes were treated with protease and then the concentrations of liposomes were determined by monitoring direct N-Rho-PE fluorescence (550 ex/590 em) and comparing with a known amount of stock liposomes. Aliquots of these fluorescently labeled protease treated liposomes were incubated with unlabeled target liposomes or cells and lipid mixing was determined as described above.

Figure 5:
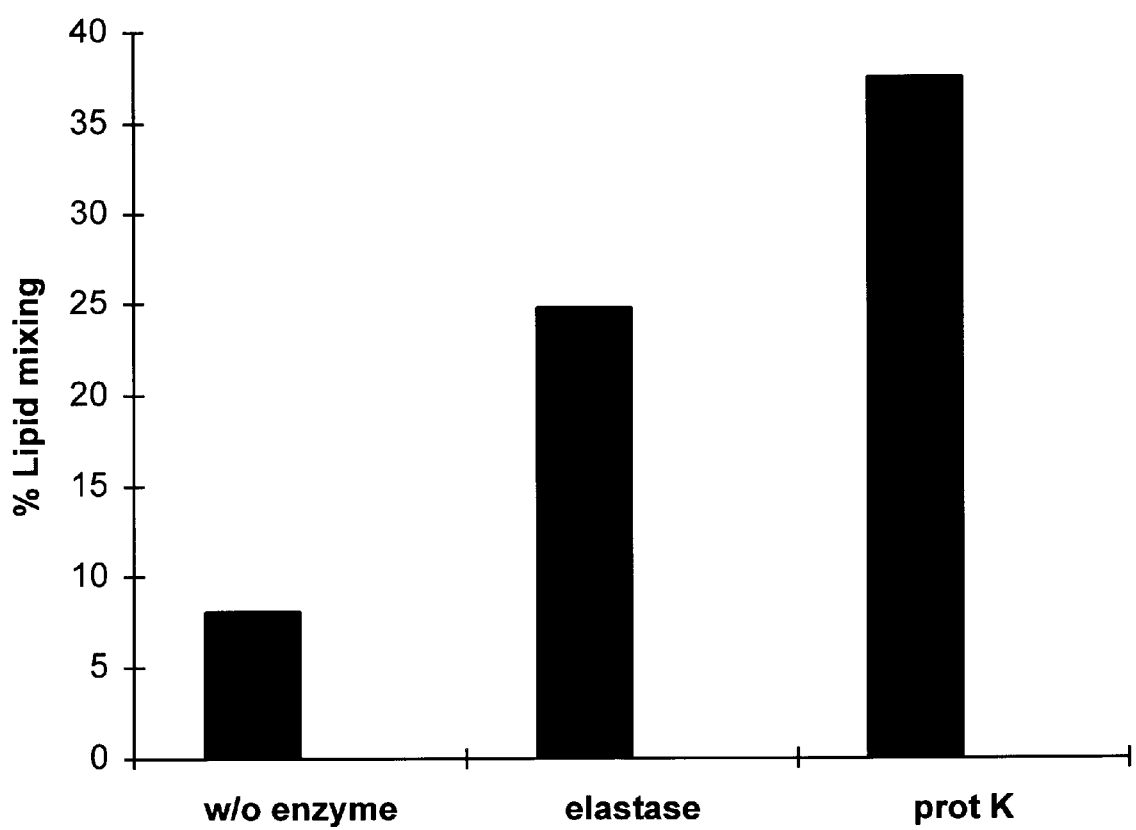
FIG. 5. Elastase and proteinase K mediated activation of liposomal fusion. DOTAP/N-Ac-AA-DOPE/PE (15/15/70 mol %) liposomes containing fluorescent membrane probes were pretreated with human leukocyte elastase or proteinase K (1 mg protein/100 nmol lipid/0.1 ml buffer) overnight at 37° C. 10 nmol aliquots were incubated with unlabeled PE/PS acceptor liposomes (80/20 mol %; 1:10 effector:acceptor ratio) for 60 min at 37° C. Lipid mixing was determined by monitoring N-NBD-PE FDQ.

Treatment by either enzyme resulted in a greater extent of lipid mixing over that of untreated liposomes (FIG. 5). This result, coupled with the shared substrate specificity of proteinase K and elastase, suggests proteinase K activation serves as a suitable substitute for elastase to characterize the fusion activation of N-Ac-AA-DOPE containing liposomes.

Figure 6:
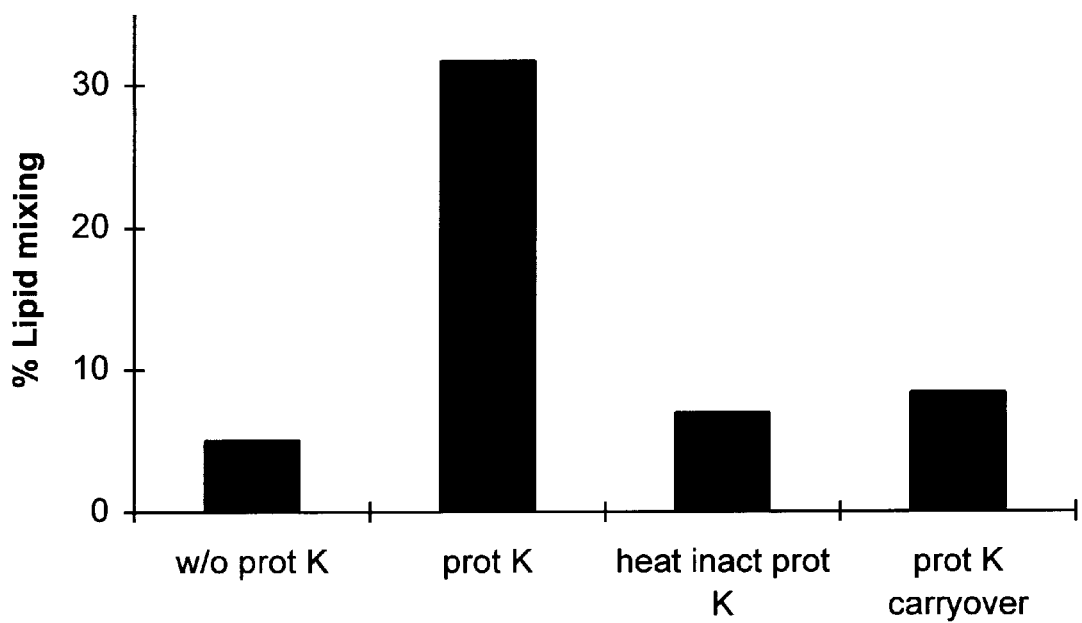
FIG. 6. Requirement for active proteinase K for DOTAP/N-Ac-M-DOPE/PE liposome fusion activation with PS/PE liposomes. DOTAP/N-Ac-AA-DOPE/PE (15/15/70 mol %) liposomes (100 nmol) containing fluorescent membrane probes were pretreated with or without 1 mg of proteinase K or heat inactivated proteinase K (1 hour, 95° C.) overnight at 37° C. in 0.1 ml buffer. 10 nmol aliquots were incubated with unlabeled PE/PS acceptor liposomes (80/20 mol %; 1:10 effector:acceptor ratio), after which lipid mixing was determined. Prot K carryover=effect of residual proteinase K carried over to incubation mixture with PE/PS liposomes was monitored by incubating untreated DOTAP/N-Ac-AA-DOPE/PE (15/15/70 mol %) liposomes with PE/PS liposomes in presence of freshly added proteinase K equivalent to the expected transferred amount.

A causal relationship between cleavage of the N-Ac-AA-DOPE peptide-lipid and fusion activation of DOTAP/N-Ac-AA-DOPE/PE liposomes was studied using heat inactivated proteinase K. DOTAP/N-Ac-M-DOPE/PE (15/15/70 mol %) liposomes containing the fluorescent membrane probes N-NBD-PE and N-Rho-PE were incubated overnight at 37° C. with active or heat inactivated proteinase K, after which an aliquot of the liposomes was incubated with unlabeled PS/PE acceptor liposomes to monitor the extent of lipid mixing. Treatment of DOTAP/N-Ac-M-DOPE/PE liposomes with active proteinase K resulted in ~30% fluorescence dequenching, a six-fold increase in lipid mixing over the untreated liposomes (FIG. 6). However, treatment with an identical amount of the heat inactivated enzyme did not activate liposomes to fuse (FIG. 6). Therefore, enzymatic activity is essential for the liposomes to become fusogenic, indicating N-Ac-AA-DOPE cleavage is crucial for triggering the fusogenic potential.

Because the experimental protocol involved transferring a small portion of active proteinase K (10 ug protease/100 nmol lipid; 100 fold dilution) along with the pretreated liposomes to the subsequent liposome-liposome incubation, it was possible that this amount of enzyme mediated the observed lipid mixing by non-specific protein effects. This possibility was tested by adding the expected carryover amount of active proteinase K to the untreated DOTAP/N-Ac-M-DOPE/PE+PE/PS incubation mixture. Lipid mixing of this sample was the same as that of liposomes incubated without proteinase K (FIG. 6). Furthermore, continuous fusion kinetics showed an immediate increase in fluorescence dequenching upon mixing of proteinase K treated DOTAP/N-Ac-AA-DOPE/PE liposomes with PS/PE liposomes (unpublished data). The enzymatically triggered threshold would presumably not be reached immediately, suggesting non-specific enzymatic cleavage of target liposomes was not responsible for fusion. The mere presence of protein cannot be responsible for fluorescence dequenching, as heat inactivated proteinase K did not mediate a similar response. Conversely, proteinase K did not physically prevent fusion, as exogenous proteinase K added to mixtures of the fusogenic DOTAP/PE liposomes with target liposomes did not inhibit lipid mixing (unpublished data). Taken together, these results indicate that only pretreatment with enzymatically active proteinase K triggers fusion of N-Ac-AA-DOPE containing liposomes.

Figure 7A:
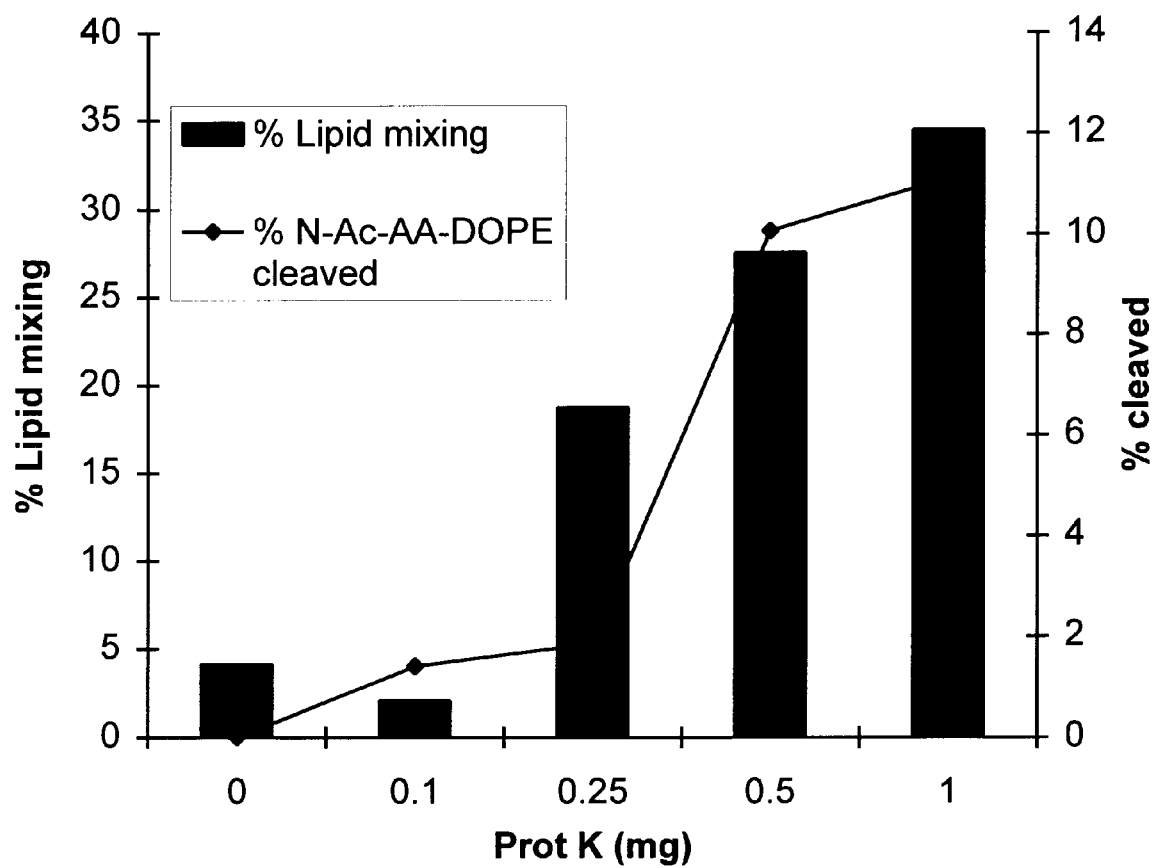
FIG. 7. Concentration and time dependence of proteinase K activity. Activation of fusion: DOTAP/N-Ac-AA-DOPE/PE (15/15/70 mol %) liposomes (100 nmol) containing fluorescent membrane probes were incubated in 0.1 ml buffer at 37° C. either overnight with given amounts of proteinase K or with 1 mg proteinase K for given times. 10 nmol aliquots were incubated with unlabeled PE/PS acceptor liposomes (80/20 mol %; 1:10 effector:acceptor ratio), after which lipid mixing was determined. N-Ac-M-DOPE cleavage: unlabeled DOTAP/N-Ac-AA-DOPE (1:1 mol ratio) liposomes were treated identically as for fusion activation, after which lipid was extracted and analyzed by HPLC (FIG. 7A depicts results of overnight incubation with proteinase K, and FIG. 7B depicts results of incubation with proteinase K for the indicated amounts of time).

The reliance of fusion activation upon enzyme cleavage of N-Ac-AA-DOPE was further assessed by examining the concentration and time dependencies of both events. DOTAP/N-Ac-M-DOPE/PE liposomes were either incubated with 0, 0.1, 0.25, 0.5, and 1 mg proteinase K/100 nmol lipid overnight, or with 1 mg proteinase K/100 nmol lipid for 1, 2, 4 hours or overnight. These liposomes were monitored for N-Ac-M-DOPE cleavage by HPLC or for lipid mixing with acceptor liposomes by N-NBD-PE fluorescence dequenching. A similar concentration dependence was evident for both N-Ac-AA-DOPE cleavage and liposome fusion (FIG. 7A). Treatment with 0.5 or 1 mg proteinase K yielded apparently maximal cleavage and fusion activity. Only background levels of both activities were observed when 0 or 0.1 mg of the enzyme were used. The kinetics of proteinase K mediated cleavage and fusion activation were also correlated, with overnight incubation giving the highest amount of cleavage and lipid mixing (FIG. 7B). These results further support the contention that the activation of fusion of DOTAP/N-Ac-AA-DOPE/PE liposomes is due to enzymatic cleavage of N-Ac-M-DOPE.

Example 9

Activation of DOTAP/N-Ac-AA-DOPE/PE fusion with RBC ghosts

Figure 8:
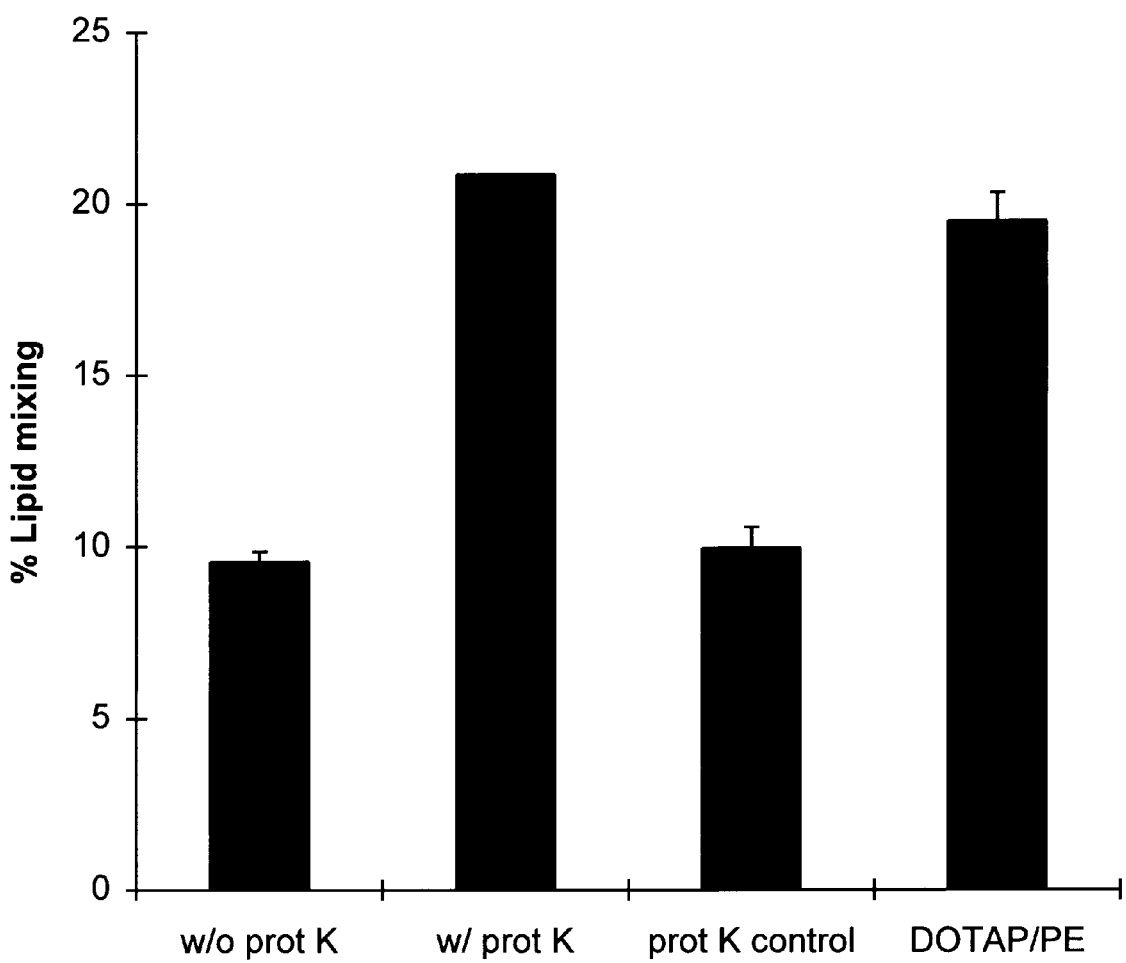
FIG. 8. Activation of DOTAP/N-Ac-AA-DOPE/PE liposomes by proteinase K for fusion with RBC ghosts. DOTAP/N-Ac-AA-DOPE/PE (20/10/70 mol %) liposomes (100 nmol) containing fluorescent membrane probes were incubated overnight at 37° C. with or without 1 mg of proteinase K in 0.1 ml buffer. 10 nmol aliquots of DOTAP/N-Ac-AA-DOPE/PE liposomes as well as DOTAP/PE (20/80 mol %) liposomes were incubated with $1 \times 10^8$ RBC ghosts in buffer containing 0.5 mM PMSF for 30 min at 37° C., after which lipid mixing was determined. Effect of transferred proteinase K on lipid mixing was monitored by incubating untreated liposomes with RBC ghosts in presence of equivalent amount of proteinase K (prot K control).
Figure 9:
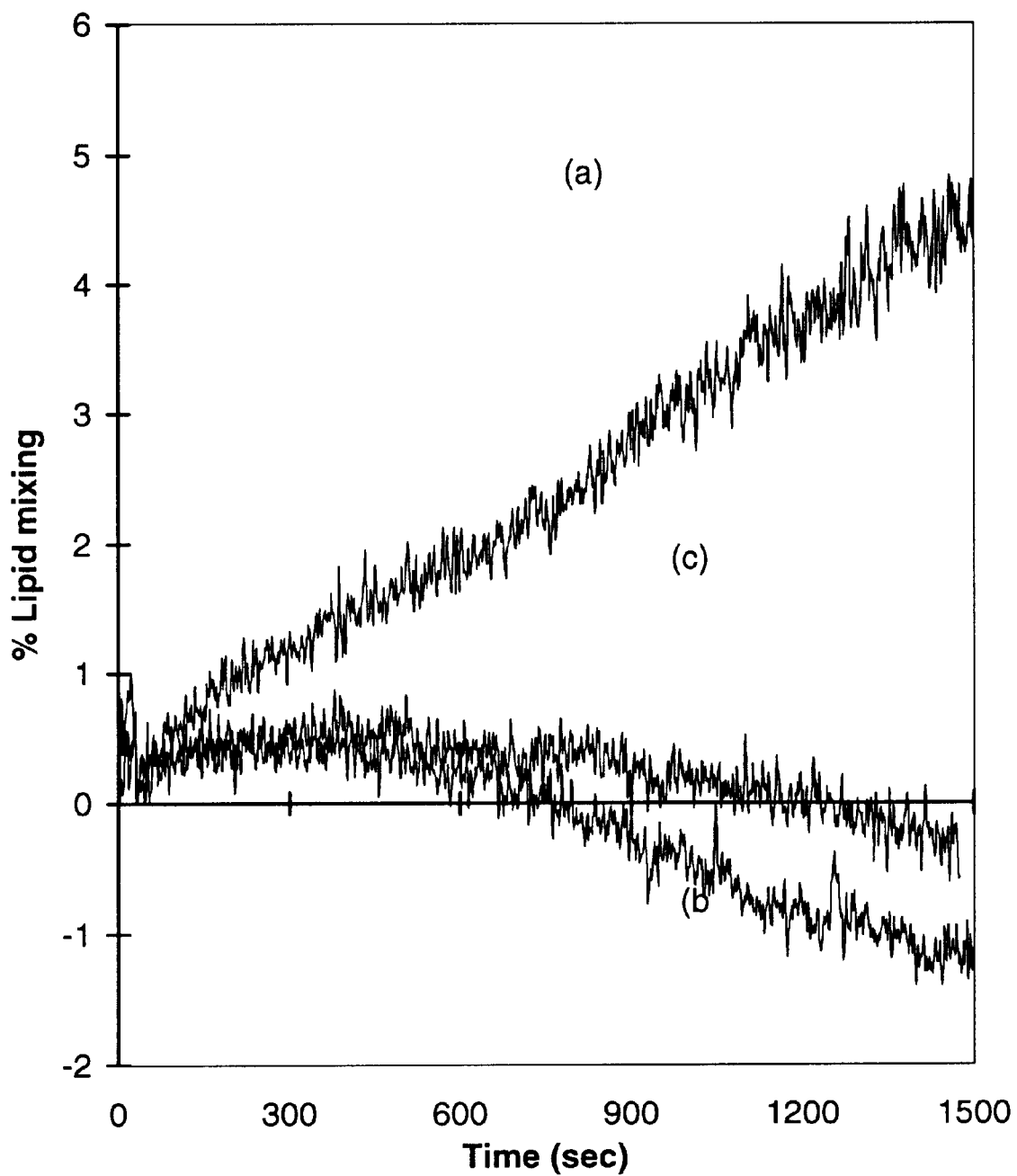
FIG. 9. DOTAP/N-Ac-M-DOPE/PE liposome with RBC ghosts: continuous kinetics of lipid mixing. 10 nmol of DOTAP/N-Ac-AA-DOPE/PE (20/10/70 mol %) liposomes incubated (a) with or (b) without proteinase K overnight at 37° C. were added to a cuvette containing 2 ml buffer with 0.5 mM PMSF under continuous stirring and 37° C. conditions. N-NBD-PE fluorescence recording was initiated and $1 \times 10^8$ RBC ghosts were added at 30 sec. (c) Effect of carryover proteinase K on lipid mixing was monitored by incubating untreated liposomes with RBC ghosts in presence of equivalent amount of proteinase K.
Figure 10A:
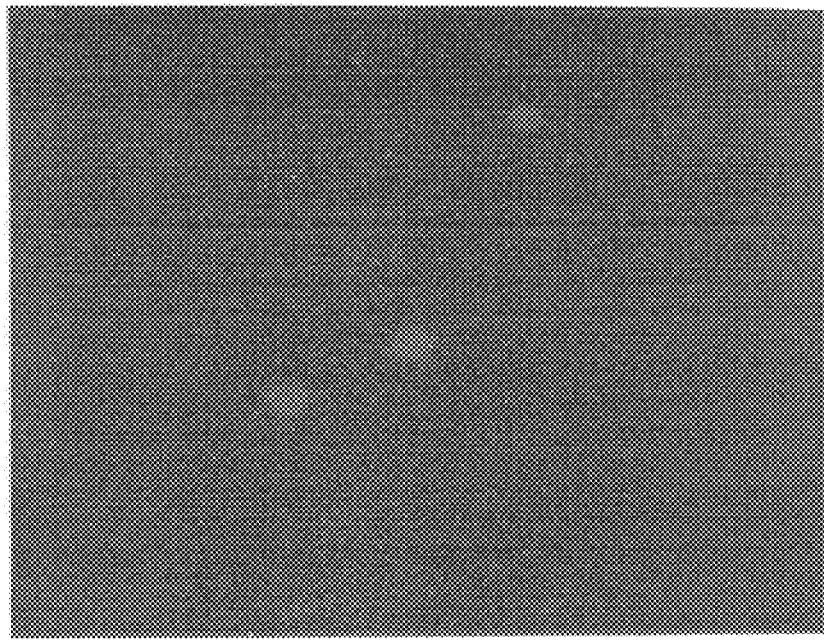
FIG. 10. Dextran loaded DOTAP/N-Ac-AA-DOPE/PE liposome fusion with RBC ghosts. DOTAP/N-Ac-M-DOPE/PE (20/10/70 mol %) liposomes were loaded with 10 kD TX-red conjugated dextrans. Liposomes were incubated with proteinase K overnight at 37° C. 40 nmol aliquots of dextran loaded liposomes (A, C) or unloaded liposomes +free dextran (B, D) were incubated with $1 \times 10^8$ RBC ghosts in 1 ml buffer for 30 min at 37° C., after which cells were washed and observed by fluorescence microscopy or Nomarski differential interference contrast microscopy (FIG. 10A depicts results with dextran-loaded liposomes, using fluorescence microscopy.
FIG. 10B depicts results with unloaded liposomes, using fluorescence microscopy.
FIG. 10C depicts results with dextran-loaded liposomes, using Nomarski contrast microscopy, FIG. 10D depicts results with unloaded liposomes using Nomarski contrast microscopy".
Figure 10B:
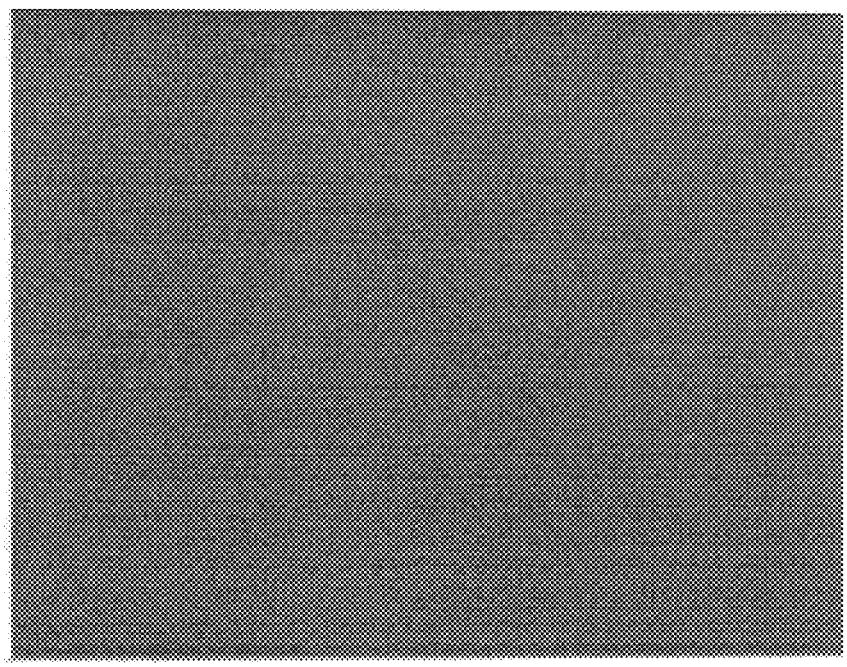
Figure 10C:
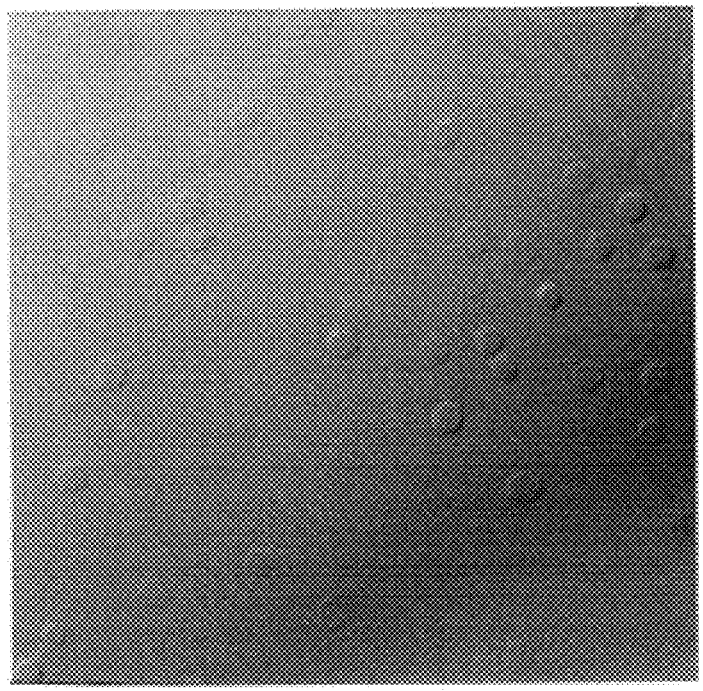
Figure 10D:
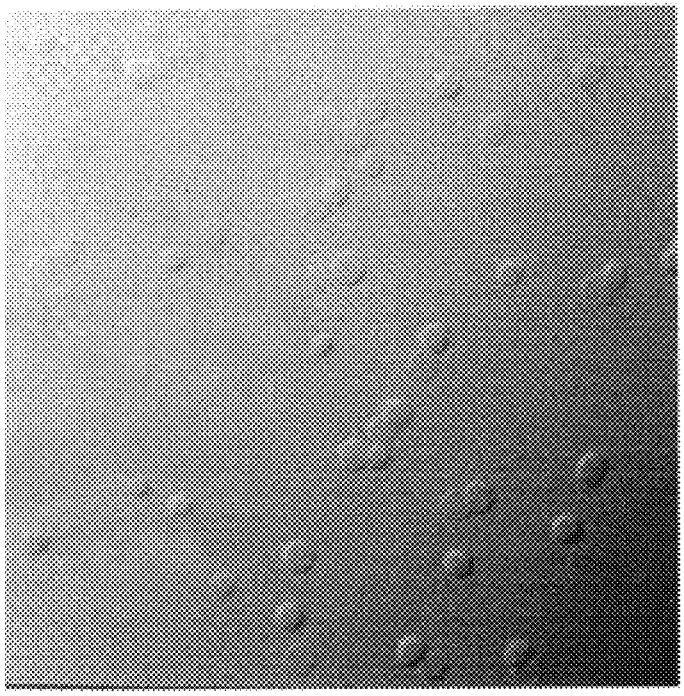

Since DOTAP/N-Ac-AA-DOPE/PE liposomes could be activated to fuse with target liposomes after enzymatic cleavage, we determined if activated fusion of N-Ac-AA-DOPE containing liposomes with cells could also be observed. As fusion with RBC ghosts (FIG. 4B) appeared to exhibit a different threshold of fusogenicity than liposomes (FIG. 4A), we prepared DOTAP/N-Ac-AA-DOPE/PE liposomes at a 20/10/70 mol ratio. The overall positive charge of these liposomes improves the binding to cells, relative to the 15/15/70 composition, without permitting the liposomes to fuse with cells in the absence of an activating trigger (FIG. 4B). After an overnight, 37° C., incubation of these liposomes with proteinase K, lipid mixing with RBC ghosts was observed in the presence of the protease inhibitor PMSF (FIG. 8). The activity of residual proteinase K transferred from the initial incubation was negligible (FIG. 8). Specific activation of DOTAP/N-Ac-AA-DOPE/PE (20/10/70 mol %) fusion with RBC ghosts was also observed under continuous kinetics conditions. Only liposomes pretreated with proteinase K were capable of fusing with RBC ghosts while untreated liposomes did not (FIG. 9). The addition of active proteinase K to untreated liposomes also did not induce fluorescence dequenching (FIG. 9, curve c), indicating the observed increase for proteinase K treated DOTAP/N-Ac-AA-DOPE/PE liposomes was due to specific fusion activation.

To determine if the lipid mixing observed after proteinase K activation was due to true fusion of liposomes with cells and not potential artifacts of the lipid mixing assay, such as membrane probe exchange or hemifusion between outer leaflet membranes, DOTAP/N-Ac-AA-DOPE/PE (20/10/70 mol %) liposomes were loaded with 10,000 MW fluorescent aqueous probe TX-red dextran. Liposomes were then treated with proteinase K and incubated with RBC ghosts. After washing the cells extensively to remove unbound liposomes the RBC ghosts were observed under fluorescence microscopy. The cell pellet was resuspended in 0.1 ml buffer and observed under an Olympus BH-2 fluorescence microscope (Olympus Corp., Lake Success, NY) using an apochromat 40× oil (N.A. 1.00) objective. TX-red fluorescence was excited by a xenon lamp transmitted through a green excitation cube (580 nm dichroic mirror, 545 nm excitation filter). Non-fluorescent images were observed with transmitted light Nomarski differential interference contrast microscopy.

Bright diffuse fluorescence could be observed in a portion of the cells (FIG. 10), indicating complete fusion occurred between liposomes and certain cells with subsequent transfer of the fluorescent aqueous probe. Differences in fluorescence levels may be due to differences in the number of liposomes fusing with a single cell. The observed fluorescence does not appear to be due to non-specific uptake of dextran out of leaky liposomes, as incubation of RBC ghosts with unlabeled liposomes and free TX-red dextran did not result in observable aqueous probe labeling (FIG. 10). Thus DOTAP/N-Ac-AA-DOPE/PE liposomes can be activated by enzymatic cleavage of the peptide-lipid to fuse with cells and deliver their aqueous contents.

Example 10

Activation of MeOSuc-Ala-Ala-Pro-Val-DOPE [SEQ ID NO:42] containing liposomes by HLE for enhanced binding/fusion 100 nmol of DOTAP/AAPV-PE (3:1; 1:1; or 1:3) were incubated +/− HLE (5 ug/100 nmol lipid) in 100 ul for 2 hours at 37 C, pH 7.4 with constant shaking. Afterwards 10 nmol of liposomes +/− HLE pretreatment were incubated with 1–2×10$^6$ HL60 (human leukemia) cells at pH 7.4 or 4. Samples were incubated 2 hours at 37 C with constant shaking. After incubation cells were washed 2 times , resuspended in 0.5 ml, and transferred to wells of Falcon 24 well plate (Primaria). Fluorescence was monitored +/− detergent in cytofluor. Liposome input (no cells) were not washed and were transferred directly to 24 well plates.

Liposomes exhibited higher binding at pH 4.0. Binding also appeared to be higher after HLE pretreatment. In addition, DODAP/AAPV-PE (1:1) may possibly exhibit higher fluorescence dequenching after HLE treatment, suggesting lipid mixing between liposomes and cells had occurred.

| DODAP/AAPV-PE | % lipo bound | | % NBD FD | |
|---|---|---|---|---|
| | pH 7.4 | pH 4.0 | pH 7.4 | pH 4.0 |
| 1:3 − HLE | 2.68 | 53.58 | 104.22 | 33.13 |
| 1:3 + HLE | 0.74 | 70.34 | −32.43 | 32.53 |
| 1:1 − HLE | 2.37 | 56.95 | 59.94 | 23.86 |
| 1:1 + HLE | 2.87 | 85.91 | 77.42 | 44.81 |
| 3:1 − HLE | 6.76 | 67.88 | −5.05 | 64.52 |
| 3:1 + HLE | 7.78 | 80.82 | 43.43 | 69.04 |

Three separate experiments also displayed enhanced binding of DODAP/AAPV-PE (1:1) to HL60 cells. One showed an enhancement from 64% to 86% fluorescence dequenching. In terms of total number of liposomes fused, HLE pretreatment appeared to enhance lipid mixing in all three experiments.

| | w/o HLE | w/HLE |
|---|---|---|
| % bound | 20.29 | 45.22 |
| # bound | 1.22E + 10 | 2.72E + 10 |
| % lipid mixing | 48.06 | 44.24 |
| # lipid mixed | 5.87E + 11 | 1.20E + 12 |
| % bound | 7.72 | 33.17 |
| # lipos bound | 4.60E + 09 | 2.00E + 10 |
| % lipid mixing | 57.12 | 25.89 |
| # lipid mixing | 2.65E + 11 | 5.17E + 11 |
| % bound | 38.09 | 46.89 |
| # Lipos bound | 2.29E + 10 | 3.08E + 10 |
| % lipid mixing | 63.74 | 86.25 |
| # lipid mixed | 1.46E + 12 | 2.43E + 12 |

REFERENCES

Aimes, R. T. and Quigley, J. P. (1995) J. Biol. Chem. 270, 5872–5876; Allen, T., et al., U.S. Pat. Nos. 4,837,028 and 4,920,016; Ascenzi et al., Anal. Biochem., 103:235 (1980); Barrett & Kirschke, Meth. Enzymol. 80:535 (1981); Bartlett, G. R., (1959) J. Biol. Chem. 234, 466–468; Berka, J. L. et al., (1996) Molecular & Cellular Endocrinology 119, 175–184; Blume et al., (1993) Biochim. Biophys. Acta. 1149:180 (1993); Boyd, D. (1996) Cancer and Metastasis Reviews 15, 77–89; Castillo et al., Anal. Biochem. 99:53 (1979); Clague, M. J., et al. (1990) Biochemistry 29, 1303–1309; Fosang, A. J., et al., (1994) Biochemical J. 304, 347–351; Froehlich, et al., (1993) J. Immunol. 151, 7161–7171; Gabizon, A., et al., Pharm. Res. 10(5):703 (1993); Hoog, S. S., et al., Biochemistry 35, 10279–10286; Johnson et al., Thromb. Diath. Haemorrh., 21:259 (1969); Kirschke et al., Biochem. J. 201:367 (1982)); Knäuper, V., et al., (1996) J. Biol. Chem. 271, 1544–1550; Knight, Biochem. J. 189:447 (1980); Kossakowska, A. E., et al., (1996) Br. J. Cancer 73, 1401–1408; Liotta, L. A., et al., (1991) Cell 64, 327–336; Mayer, L. D., et al., (1986) Biochim. Biophys. Acta 858, 161–168; Moehrle, M. C., et al., (1995) J. Cutaneous Path. 22, 241–247; Nagase, H., et al., (994) J. Biol. Chem. 269, 20952–20957; Nakajima, K., et al., (1979) J. Biol. Chem. 254, 4027–4032; Odake, S., et al., (1991) Biochemistry 30, 2217–2227; O'Leary, R. M. and O'Connor, B. (1995) Int. J. Biochem. Cell Biol. 27, 881–890; Palmieri, F. E. and Ward, P. E. (1989) Adv. Exp. Med. Biol. 247A, 305–311; Park et al., (1992) Biophys Acta. 1108:257 (1992); Pei, D., et al., (1994) J. Biol. Chem. 269, 25849–25855; Prechel, M. M., et al., (1995) J. Pharmacol. and Exp. Therapeutics 275, 1136–1142; Rogi, T., et al., (1996) J. Biol. Chem. 271, 56–61; Sato and Sunamoto, "Site Specific Liposomes Coated with Polysaccharides," in: *Liposome* Technology (G. Gregoriadis, ed.), CRC Press (Boca Raton, Fla.), 1993, pp. 179–198; Spratt, D. A., et al., (1995) Microbiology 141, 3087–3093; Steck, T. L. & Kant, J. A. (1974) Methods Enzymol. 31, 172–180; Struck, D. K., et al., (1981) Biochemistry 20, 4093–4099; Subbaro et al., Biochem. 26(11): 2964 91987); Unden, A. B., et al., (1996) J. Invest. Dermat. 107, 147–153; Vogel, S. S., Leikina, E. and Chernomordik, JBC 268: 25764 (1993); Ward, P. E., Russell, J. S. and Vaghy, P. L. (1995) Peptides 16, 1073–1078; Williamson, P., et al., (1985) J. Cell Physiol. 123, 209–214; Wilson, M. J., et al., (1993) *Biochemistry* 32, 11302–11310; Wohl et al., JBC, 255:2005 (1980); Petkov et al., Eur. J. Biochem. 51:25 (1975); Woodle et al., U.S. Pat. No. 5,013, 556; Yamashita, J. I., et al., (1994) Br. J. Cancer 69, 72–76.

What is claimed is:

1. A peptide-lipid conjugate having the formula:

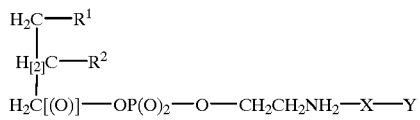

wherein:

X is a linker selected from the group consisting of a single bond and the group $R^3$; each of $R^1$, $R^2$ and $R^3$ is $-OC(O)(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$;

n1 is zero or an integer equal to from 1 to 22, n3 is zero or an integer equal to from 1 to 19, n5 is zero or an integer equal to from 1 to 16, n7 is zero or an integer equal to from 1 to 13, n9 is zero or an integer equal to from 1 to 10;

for each of $R^1$ and $R^2$ the sum of n1+2n2+n3+2n4+n5+2n6+n7+2n8+n9 is an integer equal to from 12 to 22;

for $R^3$ the sum of n1+2n2+n3+2n4+n5+2n6+n7+2n8+n9 is an integer equal to from 0 to 22, each of n2, n4, n6 and n8 is equal to 0 or 1; and, Y is an enzyme cleavable peptide comprising an amino acid sequence which is the substrate of a cell-secreted peptidase.

2. The conjugate of claim 1, wherein X is a single bond.

3. The conjugate of claim 1, wherein for each of $R^1$ and $R^2$ at least one of n2, n4, n6 and n8 is an integer equal to 1.

4. The conjugate of claim 3, wherein each of $R^1$ and $R^2$ is $-OC(O)(CH_2)_7(CH=CH)(CH_2)_7CH_3$.

5. The conjugate of claim 1, wherein the enzyme cleavable peptide comprises the amino acid sequence Ala-Ala.

6. The conjugate of claim 5, wherein the enzyme cleavable peptide comprises an amino acid sequence selected from the group consisting of the sequences Ala-Ala-, Ala-Ala-Pro-Val (SEQ ID NO:1), Ala-Ala-Met-, Ala-Ala-Pro-Phe- (SEQ ID NO:3), Ala-Ala-Pro-Met- (SEQ ID NO:4), Ala-Ala-Arg, Ser-Ala-Ala-Arg- (SEQ ID NO:5), Ser-Ser-Ala-Ala-Arg- (SEQ ID NO:6), Ser-S carboxyl sugar-Ala-Ala-Arg- (SEQ ID NO:7), Ala-Ala-Asp-, Ser-Ala-Ala-Asp- (SEQ ID NO:8) and Ser-Ser-Ala-Ala-Asp- (SEQ ID NO:9).

7. The conjugate of claim 6, wherein the enzyme cleavable peptide comprises the amino acid sequence Ala-Ala-Pro-Val (SEQ ID NO:1).

8. The conjugate of claim 1, wherein the enzyme cleavable peptide comprises an amino acid sequence selected from the group consisting of the sequences Arg-Pro-Lys-Pro-Leu-Ala-Nva- (SEQ ID NO:10), Ser-Arg-Pro-Lys-Pro-Leu-Ala-Nva- (SEQ ID NO:11), Ser-Ser-Arg-Pro-Lys-Pro-Leu-Ala-Nva (SEQ ID NO:12), Pro-Cha-Gly-Nva-His-Ala-Dpa-NH$_2$ (SEQ ID NO:13), Pro-Leu-Gly-Leu-Dpa-Ala-Arg-NH$_2$ (SEQ ID NO:14), Pro-Cha-Gly-Nva-, Pro-Leu-Gly-Leu- (SEQ ID NO:15), Gly-Pro-Arg, Leu-Pro-Arg, Glu-Gly-Arg and Gly-Pro-Gln-Gly-Ile- (SEQ ID NO:16).

9. The conjugate of claim 1, wherein the enzyme cleavable peptide is modified at its amino terminus by a moiety selected from the group consisting of acetyl, methoxy, carboxy sugar polyethylene glycol and methoxy-substituted carboxy sugar modifications.

10. The conjugate of claim 9, wherein the amino-terminal modification is by a methoxy-succinyl moiety.

11. The conjugate of claim 10, wherein the enzyme cleavable peptide comprises the modified amino acid sequence N-methoxy-succinyl-Ala-Ala-Pro-Val (SEQ ID NO:2).

12. The conjugate of claim 1 which is (SEQ ID NO:17)

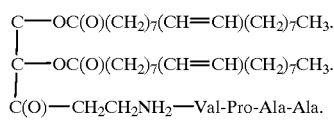

* * * * *

SEQUENCE LISTING

<160> NUMBER OF SEQ ID NOS: 44

<210> SEQ ID NO 1
<211> LENGTH: 4
<212> TYPE: PRT
<213> ORGANISM: Peptides

<400> SEQUENCE: 1

Ala Ala Pro Val
1

<210> SEQ ID NO 2
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal N-methoxysuccinyl group

```
<400> SEQUENCE: 2

Ala Ala Pro Val
 1

<210> SEQ ID NO 3
<211> LENGTH: 4
<212> TYPE: PRT
<213> ORGANISM: Peptides

<400> SEQUENCE: 3

Ala Ala Pro Phe
 1

<210> SEQ ID NO 4
<211> LENGTH: 4
<212> TYPE: PRT
<213> ORGANISM: Peptides

<400> SEQUENCE: 4

Ala Ala Pro Met
 1

<210> SEQ ID NO 5
<211> LENGTH: 4
<212> TYPE: PRT
<213> ORGANISM: Peptides

<400> SEQUENCE: 5

Ser Ala Ala Arg
 1

<210> SEQ ID NO 6
<211> LENGTH: 5
<212> TYPE: PRT
<213> ORGANISM: Peptides

<400> SEQUENCE: 6

Ser Ser Ala Ala Arg
 1               5

<210> SEQ ID NO 7
<211> LENGTH: 4
<212> TYPE: PRT
<213> ORGANISM: Peptides
<220> FEATURE:
<221> NAME/KEY: BINDING
<222> LOCATION: (1)...(2)
<223> OTHER INFORMATION: S carboxyl sugar

<400> SEQUENCE: 7

Ser Ala Ala Arg
 1

<210> SEQ ID NO 8
<211> LENGTH: 4
<212> TYPE: PRT
<213> ORGANISM: Peptides

<400> SEQUENCE: 8

Ser Ala Ala Asp
 1

<210> SEQ ID NO 9
<211> LENGTH: 5
<212> TYPE: PRT
```

```
<213> ORGANISM: Peptides

<400> SEQUENCE: 9

Ser Ser Ala Ala Asp
 1               5

<210> SEQ ID NO 10
<211> LENGTH: 7
<212> TYPE: PRT
<213> ORGANISM: Peptides
<220> FEATURE:
<221> NAME/KEY: MOD_RES
<222> LOCATION: (7)...(7)
<223> OTHER INFORMATION: Nva

<400> SEQUENCE: 10

Arg Pro Lys Pro Leu Ala Xaa
 1               5

<210> SEQ ID NO 11
<211> LENGTH: 8
<212> TYPE: PRT
<213> ORGANISM: Peptides
<220> FEATURE:
<221> NAME/KEY: MOD_RES
<222> LOCATION: (8)...(8)
<223> OTHER INFORMATION: Nva

<400> SEQUENCE: 11

Ser Arg Pro Lys Pro Leu Ala Xaa
 1               5

<210> SEQ ID NO 12
<211> LENGTH: 9
<212> TYPE: PRT
<213> ORGANISM: Peptides
<220> FEATURE:
<221> NAME/KEY: MOD_RES
<222> LOCATION: (9)...(9)
<223> OTHER INFORMATION: Nva

<400> SEQUENCE: 12

Ser Ser Arg Pro Lys Pro Leu Ala Xaa
 1               5

<210> SEQ ID NO 13
<211> LENGTH: 6
<212> TYPE: PRT
<213> ORGANISM: Peptides
<220> FEATURE:
<221> NAME/KEY: BINDING
<222> LOCATION: (1)...(2)
<223> OTHER INFORMATION: 3-cyclohexylalanyl group
<220> FEATURE:
<221> NAME/KEY: MOD_RES
<222> LOCATION: (3)...(3)
<223> OTHER INFORMATION: Nva
<220> FEATURE:
<221> NAME/KEY: VARIANT
<222> LOCATION: (6)...(6)
<223> OTHER INFORMATION: Dpa-NH2, wherein Dpa is
      N-3-(2,4-dinitrophenyl)-L-2,3-diaminopropionyl

<400> SEQUENCE: 13

Pro Gly Xaa His Ala Xaa
 1               5

<210> SEQ ID NO 14
<211> LENGTH: 7
```

```
<212> TYPE: PRT
<213> ORGANISM: Peptides
<220> FEATURE:
<221> NAME/KEY: VARIANT
<222> LOCATION: (5)...(5)
<223> OTHER INFORMATION: N-3-(2,4-dinitrophenyl)-L-2,3-diaminopropionyl
<220> FEATURE:
<221> NAME/KEY: BINDING
<222> LOCATION: (7)...(7)
<223> OTHER INFORMATION: C-terminal amino group

<400> SEQUENCE: 14

Pro Leu Gly Leu Xaa Ala Arg
  1               5

<210> SEQ ID NO 15
<211> LENGTH: 4
<212> TYPE: PRT
<213> ORGANISM: Peptides

<400> SEQUENCE: 15

Pro Leu Gly Leu
  1

<210> SEQ ID NO 16
<211> LENGTH: 5
<212> TYPE: PRT
<213> ORGANISM: Peptides

<400> SEQUENCE: 16

Gly Pro Gln Gly Ile
  1               5

<210> SEQ ID NO 17
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxysuccinyl group
<220> FEATURE:
<221> NAME/KEY: BINDING
<222> LOCATION: (4)...(4)
<223> OTHER INFORMATION: C-terminal dioleoyl phosphatidylethanolamine

<400> SEQUENCE: 17

Ala Ala Pro Val
  1

<210> SEQ ID NO 18
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal succinyl group

<400> SEQUENCE: 18

Ala Ala Pro Phe
  1

<210> SEQ ID NO 19
<211> LENGTH: 4
<212> TYPE: PRT
<213> ORGANISM: Peptides
<220> FEATURE:
<221> NAME/KEY: BINDING
```

```
<222> LOCATION: (1)...(1)
<223> OTHER INFORMATION: N-terminal methoxy succinyl group

<400> SEQUENCE: 19

Ala Ala Pro Met
 1

<210> SEQ ID NO 20
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group

<400> SEQUENCE: 20

Pro Leu Gly Leu
 1

<210> SEQ ID NO 21
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal succinyl group

<400> SEQUENCE: 21

Pro Leu Gly Leu
 1

<210> SEQ ID NO 22
<211> LENGTH: 4
<212> TYPE: PRT
<213> ORGANISM: Peptides

<400> SEQUENCE: 22

Ala Ala Pro Ala
 1

<210> SEQ ID NO 23
<211> LENGTH: 7
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group
<220> FEATURE:
<221> NAME/KEY: MOD_RES
<222> LOCATION: (7)...(7)
<223> OTHER INFORMATION: Nva

<400> SEQUENCE: 23

Arg Pro Lys Pro Leu Ala Xaa
 1               5

<210> SEQ ID NO 24
<211> LENGTH: 7
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group
<220> FEATURE:
<221> NAME/KEY: MOD_RES
```

```
<222> LOCATION: (7)...(7)
<223> OTHER INFORMATION: Nva

<400> SEQUENCE: 24

Arg Pro Lys Pro Leu Ala Xaa
 1               5

<210> SEQ ID NO 25
<211> LENGTH: 7
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal carboxy sugar group
<220> FEATURE:
<221> NAME/KEY: MOD_RES
<222> LOCATION: (7)...(7)
<223> OTHER INFORMATION: Nva

<400> SEQUENCE: 25

Arg Pro Lys Pro Leu Ala Xaa
 1               5

<210> SEQ ID NO 26
<211> LENGTH: 7
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal succinyl group
<220> FEATURE:
<221> NAME/KEY: MOD_RES
<222> LOCATION: (7)...(7)
<223> OTHER INFORMATION: Nva

<400> SEQUENCE: 26

Arg Pro Lys Pro Leu Ala Xaa
 1               5

<210> SEQ ID NO 27
<211> LENGTH: 8
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group
<220> FEATURE:
<221> NAME/KEY: MOD_RES
<222> LOCATION: (8)...(8)
<223> OTHER INFORMATION: Nva

<400> SEQUENCE: 27

Ser Arg Pro Lys Pro Leu Ala Xaa
 1               5

<210> SEQ ID NO 28
<211> LENGTH: 8
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group
<220> FEATURE:
<221> NAME/KEY: MOD_RES
<222> LOCATION: (8)...(8)
<223> OTHER INFORMATION: Nva
```

```
<400> SEQUENCE: 28

Ser Arg Pro Lys Pro Leu Ala Xaa
 1               5

<210> SEQ ID NO 29
<211> LENGTH: 9
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group
<220> FEATURE:
<221> NAME/KEY: MOD_RES
<222> LOCATION: (9)...(9)
<223> OTHER INFORMATION: Nva

<400> SEQUENCE: 29

Ser Ser Arg Pro Lys Pro Leu Ala Xaa
 1               5

<210> SEQ ID NO 30
<211> LENGTH: 9
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group
<220> FEATURE:
<221> NAME/KEY: MOD_RES
<222> LOCATION: (9)...(9)
<223> OTHER INFORMATION: Nva

<400> SEQUENCE: 30

Ser Ser Arg Pro Lys Pro Leu Ala Xaa
 1               5

<210> SEQ ID NO 31
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal carboxy sugar group

<400> SEQUENCE: 31

Ala Ala Pro Phe
 1

<210> SEQ ID NO 32
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal succinyl group

<400> SEQUENCE: 32

Ala Ala Pro Met
 1

<210> SEQ ID NO 33
<211> LENGTH: 4
<212> TYPE: PRT
<213> ORGANISM: Peptides
<220> FEATURE:
```

```
<221> NAME/KEY: BINDING
<222> LOCATION: (1)...(1)
<223> OTHER INFORMATION: N-terminal carboxy sugar group

<400> SEQUENCE: 33

Ala Ala Pro Met
 1

<210> SEQ ID NO 34
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group

<400> SEQUENCE: 34

Ser Ala Ala Arg
 1

<210> SEQ ID NO 35
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group

<400> SEQUENCE: 35

Ser Ala Ala Arg
 1

<210> SEQ ID NO 36
<211> LENGTH: 5
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group

<400> SEQUENCE: 36

Ser Ser Ala Ala Arg
 1               5

<210> SEQ ID NO 37
<211> LENGTH: 5
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group

<400> SEQUENCE: 37

Ser Ser Ala Ala Arg
 1               5

<210> SEQ ID NO 38
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group
```

-continued

```
<400> SEQUENCE: 38

Ser Ala Ala Asp
1

<210> SEQ ID NO 39
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group

<400> SEQUENCE: 39

Ser Ala Ala Asp
1

<210> SEQ ID NO 40
<211> LENGTH: 5
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal acetyl group

<400> SEQUENCE: 40

Ser Ser Ala Ala Asp
1               5

<210> SEQ ID NO 41
<211> LENGTH: 5
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal methoxy succinyl group

<400> SEQUENCE: 41

Ser Ser Ala Ala Asp
1               5

<210> SEQ ID NO 42
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal N-methoxysuccinyl group
<220> FEATURE:
<221> NAME/KEY: BINDING
<222> LOCATION: (4)...(4)
<223> OTHER INFORMATION: C-terminal dioleoyl phosphatidylethanolamine

<400> SEQUENCE: 42

Ala Ala Pro Val
1

<210> SEQ ID NO 43
<211> LENGTH: 4
<212> TYPE: PRT
<213> ORGANISM: Peptides
<220> FEATURE:
<221> NAME/KEY: BINDING
<222> LOCATION: (1)...(1)
<223> OTHER INFORMATION: N-terminal N-methoxysuccinyl group
<220> FEATURE:
```

```
<221> NAME/KEY: BINDING
<222> LOCATION: (4)...(4)
<223> OTHER INFORMATION: C-terminal phosphatidylethanolamine

<400> SEQUENCE: 43

Ala Ala Pro Val
 1

<210> SEQ ID NO 44
<211> LENGTH: 4
<212> TYPE: PRT
<213> ORGANISM: Peptides
<220> FEATURE:
<221> NAME/KEY: BINDING
<222> LOCATION: (4)...(4)
<223> OTHER INFORMATION: C-terminal dioleoyl phosphatidylethanolamine

<400> SEQUENCE: 44

Ala Ala Pro Val
 1
```